US012678442B2

(12) United States Patent (10) Patent No.: US 12,678,442 B2
Friedl et al. (45) Date of Patent: *Jul. 14, 2026

(54) DPP-IV INHIBITOR COMBINED WITH A FURTHER ANTIDIABETIC AGENT, TABLETS COMPRISING SUCH FORMULATIONS, THEIR USE AND PROCESS FOR THEIR PREPARATION

(71) Applicant: Boehringer Ingelheim International GmbH, Ingelheim am Rhein (DE)

(72) Inventors: Thomas Friedl, Schemmerhofen (DE); Michael Braun, Senden (DE); Kenji Egusa, Ikeda (JP); Hikaru Fujita, Osaka (JP); Megumi Maruyama, Hyogo (JP); Takaaki Nishioka, Kobe (JP)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/666,901

(22) Filed: May 17, 2024

(65) Prior Publication Data

US 2024/0307403 A1     Sep. 19, 2024

Related U.S. Application Data

(63) Continuation of application No. 18/345,029, filed on Jun. 30, 2023, now abandoned, which is a continuation of application No. 17/876,700, filed on Jul. 29, 2022, now abandoned, which is a continuation of application No. 17/199,569, filed on Mar. 12, 2021, now abandoned, which is a continuation of application No. 16/676,643, filed on Nov. 7, 2019, now Pat. No. 10,973,827, which is a continuation of application No. 16/007,047, filed on Jun. 13, 2018, now abandoned, which is a continuation of application No. 15/403,705, filed on Jan. 11, 2017, now Pat. No. 10,022,379, which is a continuation of application No. 15/203,906, filed on Jul. 7, 2016, now abandoned, which is a continuation of application No. 14/836,996, filed on Aug. 27, 2015, now Pat. No. 9,415,016, which is a continuation of application No. 12/935,634, filed as application No. PCT/EP2009/053978 on Apr. 2, 2009, now Pat. No. 9,155,705.

(60) Provisional application No. 61/087,343, filed on Aug. 8, 2008.

(30) Foreign Application Priority Data

Apr. 3, 2008     (EP) ..................................... 08154039

(51) Int. Cl.
| A61K 31/522 | (2006.01) |
| A61K 9/00 | (2006.01) |
| A61K 9/16 | (2006.01) |
| A61K 9/20 | (2006.01) |
| A61K 9/24 | (2006.01) |
| A61K 9/28 | (2006.01) |
| A61K 31/155 | (2006.01) |
| A61K 31/40 | (2006.01) |
| A61K 45/06 | (2006.01) |
| A61K 47/18 | (2017.01) |
| A61P 3/04 | (2006.01) |
| A61P 3/10 | (2006.01) |
| A61P 19/02 | (2006.01) |
| A61P 19/10 | (2006.01) |
| A61P 29/00 | (2006.01) |
| A61P 37/06 | (2006.01) |
| A61P 43/00 | (2006.01) |

(52) U.S. Cl.
CPC .......... *A61K 31/522* (2013.01); *A61K 9/0053* (2013.01); *A61K 9/2009* (2013.01); *A61K 9/2013* (2013.01); *A61K 9/2027* (2013.01); *A61K 9/2031* (2013.01); *A61K 9/2054* (2013.01); *A61K 9/2059* (2013.01); *A61K 9/2077* (2013.01); *A61K 9/2086* (2013.01); *A61K 9/209* (2013.01); *A61K 9/2095* (2013.01); *A61K 9/28* (2013.01); *A61K 9/2813* (2013.01); *A61K 9/282* (2013.01); *A61K 9/2866* (2013.01); *A61K 31/155* (2013.01); *A61K 45/06* (2013.01); *A61K 9/1617* (2013.01); *A61K 9/1652* (2013.01)

(58) Field of Classification Search
None
See application file for complete search history.

(56) References Cited

U.S. PATENT DOCUMENTS

| 2004/0097510 A1* | 5/2004 | Himmelsbach ........... A61P 3/10 |
| | | 514/263.21 |
| 2006/0159746 A1* | 7/2006 | Troup .................... A61P 19/04 |
| | | 514/567 |

FOREIGN PATENT DOCUMENTS

| WO | WO-2007041053 A2 * | 4/2007 | ........... A61K 31/155 |

OTHER PUBLICATIONS

Colorcon wich is retrieved from website: http://www.colorcon.com/products-formulation/all-products/film-coatings/immediate-release/opadry, published on May 20, 2015, last access date: Jun. 4, 2019. (Year: 2015).*

* cited by examiner

*Primary Examiner* — Kyung S Chang
(74) *Attorney, Agent, or Firm* — David L. Kershner

(57) ABSTRACT

The present invention relates to pharmaceutical compositions comprising fixed dose combinations of a DPP-4 inhibitor drug and a partner drug, processes for the preparation thereof, and their use to treat certain diseases.

23 Claims, No Drawings

DPP-IV INHIBITOR COMBINED WITH A FURTHER ANTIDIABETIC AGENT, TABLETS COMPRISING SUCH FORMULATIONS, THEIR USE AND PROCESS FOR THEIR PREPARATION

The present invention relates to pharmaceutical compositions comprising fixed dose combinations of a DPP-4 inhibitor drug and a partner drug, processes for the preparation thereof, and their use to treat certain diseases.

In a more detailed aspect, the present invention relates to oral solid dosage forms for fixed dose combination (FDC) of a selected dipeptidyl peptidase-4 (DPP-4) inhibitor drug and a certain partner drug. The FDC formulations are chemically stable and either a) display similarity of in-vitro dissolution profiles and/or are bioequivalent to the free combination, or b) allow to adjust the in-vitro and in-vivo performance to desired levels. In a preferred embodiment the invention relates to chemically stable FDC formulations maintaining the original dissolution profiles of corresponding mono tablets of each individual entity, with a reasonable tablet size.

The enzyme DPP-4 also known as CD26 is a serine protease known to lead to the cleavage of a dipeptide from the N-terminal end of a number of proteins having at their N-terminal end a prolin or alanin residue. Due to this property DPP-4 inhibitors interfere with the plasma level of bioactive peptides including the peptide GLP-1 and are considered to be promising drugs for the treatment of diabetes mellitus.

For example, DPP-4 inhibitors and their uses are disclosed in WO 2002/068420, WO 2004/018467, WO 2004/018468, WO 2004/018469, WO 2004/041820, WO 2004/046148, WO 2005/051950, WO 2005/082906, WO 2005/063750, WO 2005/085246, WO 2006/027204, WO 2006/029769 or WO2007/014886; or in WO 2004/050658, WO 2004/111051, WO 2005/058901, WO 2005/097798; WO 2006/068163, WO 2007/071738, WO 2008/017670; WO 2007/128721 or WO 2007/128761.

As further DPP-4 inhibitors the following compounds can be mentioned:

Sitagliptin (MK-0431) having the structural formula A below is (3R)-3-amino-1-[3-(trifluoromethyl)-5,6,7,8-tetrahydro-5H-[1,2,4]triazolo[4,3-a]pyrazin-7-yl]-4-(2,4,5-trifluorophenyl)butan-1-one, also named (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine, (A)

In one embodiment, sitagliptin is in the form of its dihydrogenphosphate salt, i.e. sitagliptin phosphate. In a further embodiment, sitagliptin phosphate is in the form of a crystalline anhydrate or monohydrate. A class of this embodiment refers to sitagliptin phosphate monohydrate. Sitagliptin free base and pharmaceutically acceptable salts thereof are disclosed in U.S. Pat. No. 6,699,871 and in Example 7 of WO 03/004498. Crystalline sitagliptin phosphate monohydrate is disclosed in WO 2005/003135 and in WO 2007/050485.

For details, e.g. on a process to manufacture this compound or a salt thereof, reference is thus made to these documents.

Vildagliptin (LAF-237) having the structural formula B below is (2S)-{[(3-hydroxyadamantan-1-yl)amino]acetyl}pyrrolidine-2-carbonitrile, also named (S)-1-[(3-hydroxy-1-adamantyl)amino]acetyl-2-cyano-pyrrolidine, (B)

Vildagliptin is specifically disclosed in U.S. Pat. No. 6,166,063 and in Example 1 of WO 00/34241. Specific salts of vildagliptin are disclosed in WO 2007/019255. A crystalline form of vildagliptin is disclosed in WO 2006/078593. A crystalline form of vildagliptin is disclosed in WO 2006/078593.

For details, e.g. on a process to manufacture this compound or a salt thereof, reference is thus made to these documents.

Saxagliptin (BMS-477118) having the structural formula C below is (1S,3S,5S)-2-{(2S)-2-amino-2-(3-hydroxyadamantan-1-yl)acetyl}-2-azabicyclo[3.1.0]hexane-3-carbonitrile, also named (S)-3-hydroxyadamantylglycine-L-cis-4,5-methanoprolinenitrile, (A)

Saxagliptin is specifically disclosed in U.S. Pat. No. 6,395,767 and in Example 60 of WO 01/68603. In one embodiment, saxagliptin is in the form of its HCl salt or its mono-benzoate salt as disclosed in WO 2004/052850. In a further embodiment, saxagliptin is in the form of the free base. In a yet further embodiment, saxagliptin is in the form of the monohydrate of the free base as disclosed in WO 2004/052850. Crystalline forms of the HCl salt and the free base of saxagliptin are disclosed in WO 2008/131149. A process for preparing saxagliptin is also disclosed in WO 2005/106011 and WO 2005/115982.

For details, e.g. on a process to manufacture this compound or a salt thereof, reference is thus made to these documents.

Denagliptin (GSK-823093) having the structural formula D below is (2S,4S)-1-[(2S)-2-amino-3,3-bis(4-fluoro-phenyl)propionyl]-4-fluoropyrrolidine-2-carbonitrile, also named (2S,4S)-4-fluoro-1-[4-fluoro-beta-(4-fluo-rophenyl)-L-phenylalanyl]-2-pyrrolidinecarbonitrile (D)

Denagliptin is specifically disclosed in U.S. Pat. No. 7,132,443 and in WO 03/002531. In one embodiment, denagliptin is in the form of its hydrochloride salt as disclosed in Example 2 of WO 03/002531 or its tosylate salt as disclosed in WO 2005/009956. A class of this embodi-ment refers to denagliptin tosylate. Crystalline anhydrous denagliptin tosylate is disclosed in WO 2005/009956.

For details, e.g. on a process to manufacture this com-pound or a salt thereof, reference is thus made to these documents.

Alogliptin (SYR-322) having the structural formula E below is 2-({6-[(3R)-3-aminopiperidin-1-yl]-3-methyl-2,4-dioxo-3,4-dihydro-2H-pyrimidin-1-yl}methyl) benzonitrile (E)

Alogliptin is specifically disclosed in US 2005/261271, EP 1586571 and in WO 2005/095381. In one embodiment, alogliptin is in the form of its benzoate salt, its hydrochloride salt or its tosylate salt each as disclosed in WO 2007/035629. A class of this embodiment refers to alogliptin benzoate. Polymorphs of alogliptin benzoate are disclosed in WO 2007/035372. A process for preparing alogliptin is disclosed in WO 2007/112368 and, specifically, in WO 2007/035629.

For details, e.g. on a process to manufacture this com-pound or a salt thereof, reference is thus made to these documents.

(S)-1-((2S,3S,11bS)-2-Amino-9,10-dimethoxy-1,3,4,7,11b-hexahydro-2H-pyrido[2,1-a]isoquinolin-3-yl)-4-fluoromethyl-pyrrolidin-2-one or a pharmaceutically acceptable salt thereof:

This compound and methods for its preparation are dis-closed in WO 2005/000848. A process for preparing this compound (specifically its dihydrochloride salt) is also disclosed in WO 2008/031749, WO 2008/031750 and WO2008/055814.

For details, e.g. on a process to manufacture this com-pound or a salt thereof, reference is thus made to these documents.

(R)-2-[6-(3-Amino-piperidin-1-yl)-3-methyl-2,4-dioxo-3,4-dihydro-2H-pyrimidin-1-ylmethyl]-4-fluoro-ben-zonitrile or a pharmaceutically acceptable salt thereof:

This compound and methods for its preparation and use are disclosed in WO 2005/095381, US 2007060530, WO 2007/033350, WO 2007/035629, WO 2007/074884, WO 2007/112368 and WO 2008/033851. Specifically claimed salts include the succinate (WO 2008/067465), benzoate, benzenesulfonate, p-toluenesulfonate, (R)-mandelate and hydrochloride. For details, e.g. on a process to manufacture this compound or a salt thereof, reference is thus made to these documents.

Partner drugs to be combined with the DPP-4 inhibitors within the pharmaceutical compositions according to this invention are biguanides (e.g. metformin such as metformin hydrochloride), thiazolidinones (e.g. pioglitazone such as pioglitazone hydrochloride), statines (e.g. atorvastatin) or ARBs (e.g. telmisartan).

The biguanide antihyperglycemic agent metformin is dis-closed in U.S. Pat. No. 3,174,901. The preparation of metformin (dimethyldiguanide) and its hydrochloride salt is state of the art and was disclosed first by Emil A. Werner and James Bell, J. Chem. Soc. 121, 1922, 1790-1794. Other pharmaceutically acceptable salts of metformin can be found in U.S. application Ser. No. 09/262,526 filed Mar. 4, 1999 or U.S. Pat. No. 3,174,901. It is preferred that the metformin employed herein be the metformin hydrochloride salt.

Unless specifically noted, in the present context the terms "DPP-4 inhibitor(s)", "biguanide(s)", "thiazolidinone(s)", "statine(s)", "ARB(s)", or any species thereof like "met-formin", "pioglitazone", are also intended to comprise any pharmaceutically acceptable salt thereof, crystal form, hydrate, solvate, diastereomer or enantiomer thereof.

For avoidance of any doubt, the disclosure of each of the foregoing documents cited above is specifically incorporated herein by reference in its entirety.

In attempts to prepare pharmaceutical compositions of selected DPP-4 inhibitors it has been observed, that the DPP-4 inhibitors with a primary or secondary amino group show incompatibilities, degradation problems, or extraction problems with a number of customary excipients such as microcrystalline cellulose, sodium starch glycolate, croscarmellose sodium, tartaric acid, citric acid, glucose, fructose, saccharose, lactose, maltodextrines. Though the compounds themselves are very stable, they react with incompatible partner drug, or its impurity product, and/or with many excipients used in solid dosage forms and with impurities of excipients, especially in tight contact provided in tablets and at high excipient/drug ratios. The amino group appears to react with reducing sugars and with other reactive carbonyl groups and with carboxylic acid functional groups formed for example at the surface of microcrystalline cellulose by oxidation. These unforeseen difficulties are primarily observed in low dosage ranges of the DPP-4 inhibitor used, which are required due to their surprising potency, and/or high dosage ranges of the partner drug used. Thus, pharmaceutical compositions are required to solve these technical problems, which may be associated with the unexpected potency of selected DPP-4 inhibitor compounds.

Other aims of the present invention will become apparent to the skilled man from the foregoing and following remarks.

It has now been found that the pharmaceutical compositions, which are described in greater details herein, have surprising and particularly advantageous properties.

In particular, it has been found that by the use of a nucleophilic and/or basic agent, which may be suitable for stabilizing, such as e.g. a suitable buffering agent as stabilizer, within these pharmaceutical compositions one can overcome these problems, e.g. of incompatibility and poor stability, especially decomposition and/or "assay decrease" which may be caused e.g. by reaction (e.g. by acylation, urea formation or Maillard reaction, or the like) of free base type DPP-4 inhibitors when combined with an incompatible partner drug, or its impurity product and/or a pharmaceutical excipient having such functional group (such as a reducing end of a sugar or an acyl group, such as e.g. an acetyl or carbamoyl group) to form derivatives with the free base type DPP-4 inhibitors, such as e.g. N-acetyl or N-carbamoyl derivatives. Therefore, by the use of a suitable nucleophilic and/or basic agent (e.g. a buffering and/or pH modifying agent) within these pharmaceutical compositions protection against decomposition and degradation can be achieved.

Thus, the present invention is directed to a chemically stable FDC formulation comprising a DPP-4 inhibitor, a partner drug, and a nucleophilic and/or basic agent.

Thus, the present invention is also directed to a chemically stable FDC formulation comprising a DPP-4 inhibitor, a partner drug, and a suitable buffering agent.

Thus, the present invention is also directed to a chemically stable FDC formulation comprising a DPP-4 inhibitor, a partner drug, and a pH modifying agent.

A DPP-4 inhibitor within the meaning of the present invention includes, without being limited to, any of those DPP-4 inhibitors mentioned hereinabove and hereinbelow, preferably orally active DPP-4 inhibitors.

In a closer embodiment, a DPP-4 inhibitor within the meaning of the present invention includes a DPP-4 inhibitor with an amino group, especially a free or primary amino group.

In a yet closer embodiment, a DPP-4 inhibitor in the context of the present invention is a DPP-4 inhibitor with a primary amino group, particularly with a free primary amino group.

The partner drug used is selected from the group consisting of a biguanide (e.g. metformin such as metformin hydrochloride), a thiazolidinone (e.g. pioglitazone such as pioglitazone hydrochloride), a statine (e.g. atorvastatin) and an ARB (e.g. telmisartan). A preferred partner drug within the meaning of this invention is metformin, particularly metformin hydrochloride (1,1-dimethylbiguanide hydrochloride or metformin HCl).

The buffering agent used may be a basic amino acid, which has an intramolecular amino group and alkaline characteristics (isoelectric point, pI: 7.59-10.76), such as e.g. L-arginine, L-lysine or L-histigine. A preferred buffering agent within the meaning of this invention is L-arginine. L-Arginine has a particular suitable stabilizing effect on the compositions of this invention, e.g. by suppressing degradation of the DPP-4 inhibitor in the presence of the partner drug.

The present invention is directed to a pharmaceutical comprising a DPP-4 inhibitor, a partner drug, a nucleophilic and/or basic agent, and one or more pharmaceutical excipients.

The present invention is also directed to a pharmaceutical composition comprising a DPP-4 inhibitor, a partner drug, a suitable buffering agent, and one or more pharmaceutical excipients.

The present invention is also directed to a pharmaceutical comprising a DPP-4 inhibitor, a partner drug, a pH modifying agent, and one or more pharmaceutical excipients.

In an embodiment, the present invention is directed to a pharmaceutical composition (e.g. an oral solid dosage form, particularly a tablet) comprising a DPP-4 inhibitor; a partner drug (particularly metformin); and L-arginine for stabilizing the composition and/or the DPP-4 inhibitor, particularly against chemical degradation; as well as one or more pharmaceutical excipients.

In another embodiment, the present invention is directed to a pharmaceutical composition (e.g. an oral solid dosage form, particularly a tablet) obtainable from a DPP-4 inhibitor; a partner drug (particularly metformin); and L-arginine for stabilizing the composition and/or the DPP-4 inhibitor, particularly against chemical degradation; as well as one or more pharmaceutical excipients.

In general, pharmaceutical excipients which may be used may be selected from the group consisting of one or more fillers, one or more binders or diluents, one or more lubricants, one or more disintegrants, and one or more glidants, one or more film-coating agents, one or more plasticizers, one or more pigments, and the like.

The pharmaceutical compositions (tablets) of this invention comprise usually a binder.

In more detail, the pharmaceutical compositions (tablets) of this invention comprise usually one or more fillers (e.g. D-mannitol, corn starch and/or pregelatinized starch), a binder (e.g. copovidone), a lubricant (e.g. magnesium stearate), and a glidant (e.g. colloidal anhydrous silica).

Suitably the pharmaceutical excipients used within this invention are conventional materials such as D-mannitol, corn starch, pregelatinized starch as a filler, copovidone as a binder, magnesium stearate as a lubricant, colloidal anhydrous silica as a glidant, hypromellose as a film-coating agent, propylene glycol as a plasticizer, titanium dioxide, iron oxide red/yellow as a pigment, and talc, etc.

A typical composition according to the present invention comprises the binder copovidone (also known as copolyvidone or Kollidon VA64).

Further, a typical composition according to the present invention comprises the filler corn starch, the binder copovidone, the lubricant magnesium stearate, and the glidant colloidal anhydrous silica.

A pharmaceutical composition according to an embodiment of the present invention is intended for the treatment of diabetes and/or to achieve glycemic control in a type 1 or type 2 diabetes mellitus patient and comprises a fixed dose combination formulation as described herein together with suitable pharmaceutical excipients. Additionally the compositions can be used to treat rheumatoid arthritis, obesity and osteoporosis as well as to support allograft transplantation.

Thus, in particular, the present invention is directed to a pharmaceutical composition (especially an oral solid dosage form, particularly a tablet) comprising a DPP-4 inhibitor, metformin hydrochloride, L-arginine and one or more pharmaceutical excipients, particularly one or more fillers, one or more binders, one or more glidants, and/or one or more lubricants.

In more particular, the present invention is directed to a pharmaceutical composition (especially an oral solid dosage form, particularly a tablet) comprising a DPP-4 inhibitor, metformin hydrochloride, L-arginine, copovidone as binder and one or more further pharmaceutical excipients.

Typical pharmaceutical compositions of this invention may comprise in the DPP-4 inhibitor portion 0.1-10% L-arginine (such as e.g. about 0.1%, 0.25%, 0.556%, 2.12%, 2.22% or 10%) by weight of total DPP-4 inhibitor portion, particularly about 2% (e.g. more specifically, 2.12% by weight of total tablet core of uncoated monolayer tablet).

Typical pharmaceutical compositions of this invention may comprise in the DPP-4 inhibitor portion (% by weight of total DPP-4 inhibitor portion):

0.2-10% DPP-4 inhibitor, and
0.1-10% L-arginine.

Typical pharmaceutical compositions of this invention may comprise the DPP-4 inhibitor and L-arginine in a weight ratio of from about 1:20 to about 10:1 or from about 1:15 to about 10:1 or from about 1:10 to about 10:1, especially from 1:10 to 5:2, such as e.g. in a weight ratio of 1:10, 1:8.5, 1:5, 1:1, or 1:0.4, more detailed in a weight ratio of 2.5 mg:25 mg, 2.5 mg:21.2 mg, 2.5 mg:12.5 mg, 2.5 mg:2.5 mg, or 2.5 mg:1 mg.

Typical pharmaceutical compositions of this invention may comprise metformin hydrochloride and L-arginine in a weight ratio of from about 40:1 to about 1000:1, such as e.g. in a weight ratio of 40:1, 200:1, 340:1, 400:1, 500:1, 850:1, or 1000:1, more detailed in a weight ratio of 500 mg:12.5 mg, 850 mg:21.2 mg, 1000 mg:25 mg, 500 mg:2.5 mg, 850 mg:2.5 mg, 1000 mg:2.5 mg, 500 mg:1 mg, 850 mg:1 mg, or 1000 mg:1 mg.

Typical pharmaceutical compositions of this invention may comprise the DPP4-inhibitor, metformin hydrochloride and L-arginine in a weight ratio of from about 1:200:0.4 to about 1:200:5 (e.g. 1:200:0.4, 1:200:1, 1:200:5), or from about 1:340:0.4 to about 1:340:8.5 (e.g. 1:340:0.4, 1:340:1, 1:340:8.5), or from about 1:400:0.4 to about 1:400:10 (e.g. 1:400:0.4, 1:400:1, 1:400:10).

Typical pharmaceutical compositions of this invention may comprise one or more of the following amounts (% by weight of total coated tablet mass):

| | |
|---|---|
| 0.1-0.5% | DPP-4 inhibitor, |
| 47-85% | metformin HCl, |
| 0.07-2.2% | L-arginine, |
| 3.9-8.1% | binder (e.g. copovidone), |
| 2.3-5.9% | filler 1 (e.g. corn starch), |
| 0-4.4% | filler 2 (e.g. pregelatinized starch), |
| 0-33% | filler 3 (e.g. D-mannitol), |
| 0.7-1.5% | lubricant (e.g. magnesium stearate), and |
| 0.1-0.5% | glidant (e.g. colloidal anhydrous silica). |

Further details about the FDC formulations of this invention, e.g. the ingredients, ratio of ingredients (such as e.g. ratio of DPP-4 inhibitor, metformin hydrochloride, L-arginine and/or excipients), particularly with respect to special dosage forms (tablets) used within this invention as well as their preparation, become apparent to the skilled person from the disclosure hereinbefore and hereinafter (including by way of example the following examples as well as the claims).

In a first embodiment (embodiment A), a DPP-4 inhibitor in the context of the present invention is any DPP-4 inhibitor of formula (I)

(I)

or formula (II)

(II)

or formula (III)

(III)

wherein R1 denotes ([1,5]naphthyridin-2-yl)methyl, (quinazolin-2-yl)methyl, (quinoxalin-6-yl)methyl, (4-methyl-quinazolin-2-yl)methyl, 2-cyano-benzyl, (3-cyano-quinolin-2-yl)methyl, (3-cyano-pyridin-2-yl)methyl, (4-methyl-pyrimidin-2-yl)methyl, or (4,6-dimethyl-pyrimidin-2-yl) methyl and R2 denotes 3-(R)-amino-piperidin-1-yl, (2-amino-2-methyl-propyl)-methylamino or (2-(S)-amino-propyl)-methylamino, or its pharmaceutically acceptable salt;

In a second embodiment (embodiment B), a DPP-4 inhibitor in the context of the present invention is a DPP-4 inhibitor selected from the group consisting of sitagliptin, vildagliptin, saxagliptin and alogliptin, or its pharmaceutically acceptable salt.

Regarding the first embodiment (embodiment A), preferred DPP-4 inhibitors are any or all of the following compounds and their pharmaceutically acceptable salts:

1-[(4-methyl-quinazolin-2-yl)methyl]-3-methyl-7-(2-butyn-1-yl)-8-(3-(R)-amino-piperidin-1-yl)-xanthine (compare WO 2004/018468, example 2(142):

1-[([1,5]naphthyridin-2-yl)methyl]-3-methyl-7-(2-butyn-1-yl)-8-((R)-3-amino-piperidin-1-yl)-xanthine (compare WO 2004/018468, example 2(252)):

1-[(Quinazolin-2-yl)methyl]-3-methyl-7-(2-butyn-1-yl)-8-((R)-3-amino-piperidin-1-yl)-xanthine (compare WO 2004/018468, example 2(80)):

2-((R)-3-Amino-piperidin-1-yl)-3-(but-2-yinyl)-5-(4-methyl-quinazolin-2-ylmethyl)-3,5-dihydro-imidazo[4,5-d]pyridazin-4-one (compare WO 2004/050658, example 136):

1-[(4-Methyl-quinazolin-2-yl)methyl]-3-methyl-7-(2-butyin-1-yl)-8-[(2-amino-2-methyl-propyl)-methyl-amino]-xanthine (compare WO 2006/029769, example 2(1)):

1-[(3-Cyano-quinolin-2-yl)methyl]-3-methyl-7-(2-butyn-1-yl)-8-((R)-3-amino-piperidin-1-yl)-xanthine (compare WO 2005/085246, example 1(30)):

1-(2-Cyano-benzyl)-3-methyl-7-(2-butyn-1-yl)-8-((R)-3-amino-piperidin-1-yl)-xanthine (compare WO 2005/085246, example 1(39):

1-[(4-Methyl-quinazolin-2-yl)methyl]-3-methyl-7-(2-butyn-1-yl)-8-[(S)-(2-amino-propyl)-methylamino]-xanthine (compare WO 2006/029769, example 2(4)):

1-[(3-Cyano-pyridin-2-yl)methyl]-3-methyl-7-(2-butyn-1-yl)-8-((R)-3-amino-piperidin-1-yl)-xanthine (compare WO 2005/085246, example 1(52)):

11 | 12

1-[(4-Methyl-pyrimidin-2-yl)methyl]-3-methyl-7-(2-butyn-1-yl)-8-((R)-3-amino-piperidin-1-yl)-xanthine (compare WO 2005/085246, example 1(81)):

1-[(4,6-Dimethyl-pyrimidin-2-yl)methyl]-3-methyl-7-(2-butyn-1-yl)-8-((R)-3-amino-piperidin-1-yl)-xanthine (compare WO 2005/085246, example 1(82)):

1-[(Quinoxalin-6-yl)methyl]-3-methyl-7-(2-butyn-1-yl)-8-((R)-3-amino-piperidin-1-yl)-xanthine (compare WO 2005/085246, example 1(83)):

These DPP-4 inhibitors are distinguished from structurally comparable DPP-4 inhibitors, as they combine exceptional potency and a long-lasting effect with favourable pharmacological properties, receptor selectivity and a favourable side-effect profile or bring about unexpected therapeutic advantages or improvements when combined with other pharmaceutical active substances. Their preparation is disclosed in the publications mentioned.

A more preferred DPP-4 inhibitor among the abovementioned DPP-4 inhibitors of embodiment A of this invention is 1-[(4-methyl-quinazolin-2-yl)methyl]-3-methyl-7-(2-butyn-1-yl)-8-(3-(R)-amino-piperidin-1-yl)-xanthine, particularly the free base thereof (which is also known as BI 1356).

Regarding the second embodiment (embodiment B), preferred DPP-4 inhibitors are selected from the group consisting of vildagliptin, saxagliptin and alogliptin, and their pharmaceutically acceptable salts.

Unless otherwise noted, according to this invention it is to be understood that the definitions of the above listed DPP-4 inhibitors also comprise their pharmaceutically acceptable salts as well as hydrates, solvates and polymorphic forms thereof. With respect to salts, hydrates and polymorphic forms thereof, particular reference is made to those which are referred to hereinabove and hereinbelow.

With respect to embodiment A, the methods of synthesis for the DPP-4 inhibitors according to embodiment A of this invention are known to the skilled person. Advantageously, the DPP-4 inhibitors according to embodiment A of this invention can be prepared using synthetic methods as described in the literature. Thus, for example, purine derivatives of formula (I) can be obtained as described in WO 2002/068420, WO 2004/018468, WO 2005/085246, WO 2006/029769 or WO 2006/048427, the disclosures of which are incorporated herein. Purine derivatives of formula (II) can be obtained as described, for example, in WO 2004/050658 or WO 2005/110999, the disclosures of which are incorporated herein. Purine derivatives of formula (III) can be obtained as described, for example, in WO 2006/068163, WO 2007/071738 or WO 2008/017670, the disclosures of which are incorporated herein. The preparation of those DPP-4 inhibitors, which are specifically mentioned hereinabove, is disclosed in the publications mentioned in connection therewith. Polymorphous crystal modifications and formulations of particular DPP-4 inhibitors are disclosed in WO 2007/128721 and WO 2007/128724, respectively, the disclosures of which are incorporated herein in their entireties.

With respect to embodiment B, the methods of synthesis for the DPP-4 inhibitors of embodiment B are described in the scientific literature and/or in published patent documents, particularly in those cited herein.

With respect to the first embodiment (embodiment A), the dosage typically required of the DPP-4 inhibitors mentioned herein in embodiment A when administered orally is 0.5 mg to 100 mg, preferably 2.5 mg to 50 mg or 0.5 mg to 10 mg, more preferably 2.5 mg to 10 mg or 1 mg to 5 mg, in each case 1 to 4 times a day. Thus, the dosage required of 1-[(4-methyl-quinazolin-2-yl)methyl]-3-methyl-7-(2-butyn-1-yl)-8-(3-(R)-amino-piperidin-1-yl)-xanthine when administered orally is 0.5 mg to 10 mg per patient per day, preferably 2.5 mg to 10 mg or 1 mg to 5 mg per patient per day.

A dosage form prepared with a pharmaceutical composition comprising a DPP-4 inhibitor mentioned herein in embodiment A contain the active ingredient in a dosage range of 0.1-100 mg, in particular 0.5 to 10 mg. Thus, particular dosage strengths of 1-[(4-methyl-quinazolin-2-yl)methyl]-3-methyl-7-(2-butyn-1-yl)-8-(3-(R)-amino-piperidin-1-yl)-xanthine are 0.5 mg, 1 mg, 2.5 mg, 5 mg and 10 mg. A more particular unit dosage strength of 1-[(4-methyl-quinazolin-2-yl)methyl]-3-methyl-7-(2-butyn-1-yl)-8-(3-(R)-amino-piperidin-1-yl)-xanthine for inclusion into fixed dose combination pharmaceutical compositions of the present invention is 2.5 mg.

With respect to the second embodiment (embodiment B), the doses of DPP-4 inhibitors mentioned herein in embodiment B to be administered to mammals, for example human beings, of, for example, approximately 70 kg body weight, may be generally from about 0.5 mg to about 350 mg, for example from about 10 mg to about 250 mg, preferably 20-200 mg, more preferably 20-100 mg, of the active moiety per person per day, or from about 0.5 mg to about 20 mg, preferably 2.5-10 mg, per person per day, divided preferably into 1 to 4 single doses which may, for example, be of the same size. Single dosage strengths comprise, for example, 2.5, 5, 10, 25, 40, 50, 75, 100, 150 and 200 mg of the DPP-4 inhibitor active moiety.

A dosage strength of the DPP-4 inhibitor sitagliptin is usually between 25 and 200 mg of the active moiety. A recommended dose of sitagliptin is 100 mg calculated for the active moiety (free base anhydrate) once daily. Unit dosage strengths of sitagliptin free base anhydrate (active moiety) are 25, 50, 75, 100, 150 and 200 mg. Particular unit dosage strengths of sitagliptin (e.g. per tablet) are 25, 50 and 100 mg. An equivalent amount of sitagliptin phosphate monohydrate to the sitagliptin free base anhydrate is used in the pharmaceutical compositions, namely, 32.13, 64.25, 96.38, 128.5, 192.75, and 257 mg, respectively. Adjusted dosages of 25 and 50 mg sitagliptin are used for patients with renal failure.

A dosage range of the DPP-4 inhibitor vildagliptin is usually between 10 and 150 mg daily, in particular between 25 and 150 mg, 25 and 100 mg or 25 and 50 mg or 50 and 100 mg daily. Particular examples of daily oral dosage are 25, 30, 35, 45, 50, 55, 60, 80, 100 or 150 mg. In a more particular aspect, the daily administration of vildagliptin is between 25 and 150 mg or between 50 and 100 mg. In another more particular aspect, the daily administration of vildagliptin is 50 or 100 mg. The application of the active ingredient may occur up to three times a day, preferably one or two times a day. Particular dosage strengths are 50 mg or 100 mg vildagliptin.

Metformin is usually given in doses varying from about 250 mg to 3000 mg, particularly from 500 mg to 2000 mg up to 2500 mg per day using various dosage regimens. A dosage range of the partner drug metformin is usually from 100 mg to 500 mg or 200 mg to 850 mg (1-3 times a day), or from 300 mg to 1000 mg once or twice a day. The unit dosage strengths of the metformin hydrochloride for use in the present invention may be from 100 mg to 2000 mg or from 250 mg to 2000 mg, preferably from 250 mg to 1000 mg. Particular dosage strengths may be 250, 500, 625, 750, 850 and 1000 mg of metformin hydrochloride. These unit dosage strengths of metformin hydrochloride represent the dosage strengths approved in the US for marketing to treat type 2 diabetes. More particular unit dosage strengths of metformin hydrochloride for incorporation into the fixed dose combination pharmaceutical compositions of the present invention are 500, 850 and 1000 mg of metformin hydrochloride.

A dosage of the partner drug pioglitazone is usually 1-10 mg, 15 mg, 30 mg, or 45 mg once a day.

A dosage of the partner drug telmisartan is usually from 20 mg to 320 mg or 40 mg to 160 mg per day.

A dosage of the partner drug atorvastatin is usually from 1 mg to 40 mg or 10 mg to 80 mg once a day.

The amount of the DPP-4 inhibitor and of the partner drug in the pharmaceutical composition according to this invention correspond to the respective dosage ranges as provided hereinbefore. For example, a pharmaceutical composition comprises 1-[(4-methyl-quinazolin-2-yl)methyl]-3-methyl-7-(2-butyn-1-yl)-8-(3-(R)-amino-piperidin-1-yl)-xanthine in an amount of 0.5 mg to 10 mg (namely 0.5 mg, 1 mg, 2.5 mg, 5 mg or 10 mg) and of metformin hydrochloride in an amount of 250 mg to 1000 mg (namely 250, 500, 625, 750, 850 or 1000 mg).

Specific embodiments of dosage strengths for 1-[(4-methyl-quinazolin-2-yl)methyl]-3-methyl-7-(2-butyn-1-yl)-8-(3-(R)-amino-piperidin-1-yl)-xanthine and metformin hydrochloride in the fixed dose combinations of the present invention are the following:

(1) 2.5 mg of 1-[(4-methyl-quinazolin-2-yl)methyl]-3-methyl-7-(2-butyn-1-yl)-8-(3-(R)-amino-piperidin-1-yl)-xanthine free base, and 500 mg metformin hydrochloride;

(2) 2.5 mg of 1-[(4-methyl-quinazolin-2-yl)methyl]-3-methyl-7-(2-butyn-1-yl)-8-(3-(R)-amino-piperidin-1-yl)-xanthine free base, and 850 mg metformin hydrochloride;

(3) 2.5 mg of 1-[(4-methyl-quinazolin-2-yl)methyl]-3-methyl-7-(2-butyn-1-yl)-8-(3-(R)-amino-piperidin-1-yl)-xanthine free base, and 1000 mg metformin hydrochloride.

The particular fixed dose combinations of BI 1356 and metformin of the present invention may be administered once or twice daily to the patient, in particular twice daily.

In a preferred aspect of the present invention, the present invention is directed to a pharmaceutical composition (especially an oral solid dosage form, particularly a tablet) comprising or obtainable from a DPP-4 inhibitor selected from the group consisting of 1-[(4-methyl-quinazolin-2-yl)methyl]-3-methyl-7-(2-butyn-1-yl)-8-(3-(R)-amino-piperidin-1-yl)-xanthine free base, vildagliptin, saxagliptin and alogliptin, metformin hydrochloride, L-arginine, and one or more pharmaceutical excipients, such as e.g. those described herein.

A particularly preferred DPP-4 inhibitor to be emphasized within the meaning of this invention is 1-[(4-methyl-quinazolin-2-yl)methyl]-3-methyl-7-(2-butyn-1-yl)-8-(3-(R)-amino-piperidin-1-yl)-xanthine free base (also known as BI 1356).

In particular, it has been found that L-arginine is effective as stabilizing agent for FDC combinations of 1-[(4-methyl-quinazolin-2-yl)methyl]-3-methyl-7-(2-butyn-1-yl)-8-(3-(R)-amino-piperidin-1-yl)-xanthine free base with metformin HCl. Even after 6 months storage at accelerated conditions L-arginine is able to suppress degradation of 1-[(4-methyl-quinazolin-2-yl)methyl]-3-methyl-7-(2-butyn-1-yl)-8-(3-(R)-amino-piperidin-1-yl)-xanthine free base effectively. The effect seems to be concentration dependent. Thus, L-arginine may act as stabilizing and buffering agent in the formulation.

In a more preferred aspect of the present invention, the present invention is directed to a pharmaceutical composition (especially an oral solid dosage form, particularly a tablet) comprising or made from 1-[(4-methyl-quinazolin-2-yl)methyl]-3-methyl-7-(2-butyn-1-yl)-8-(3-(R)-amino-piperidin-1-yl)-xanthine free base (BI 1356), metformin hydrochloride, L-arginine, and one or more pharmaceutical excipients, such as e.g. those described herein.

Typical pharmaceutical compositions according to this invention comprise or are made by comprising combining any one of the following amounts (1), (2) or (3) of active ingredients and L-arginine:

(1) 2.5 mg of 1-[(4-methyl-quinazolin-2-yl)methyl]-3-methyl-7-(2-butyn-1-yl)-8-(3-(R)-amino-piperidin-1-yl)-xanthine free base, 500 mg metformin hydrochloride, and from 1.0 mg to 12.5 mg L-arginine (specifically 1.0 mg, 2.5 mg or 12.5 mg L-arginine);

(2) 2.5 mg of 1-[(4-methyl-quinazolin-2-yl)methyl]-3-methyl-7-(2-butyn-1-yl)-8-(3-(R)-amino-piperidin-1-yl)-xanthine free base, 850 mg metformin hydrochloride, and from 1.0 mg to 21.2 mg L-arginine (specifically 1.0 mg, 2.5 mg or 21.2 mg L-arginine);

(3) 2.5 mg of 1-[(4-methyl-quinazolin-2-yl)methyl]-3-methyl-7-(2-butyn-1-yl)-8-(3-(R)-amino-piperidin-1-yl)-xanthine free base, 1000 mg metformin hydrochloride, and from 1.0 mg to 25.0 mg L-arginine (specifically 1.0 mg, 2.5 mg or 25 mg L-arginine).

In a further aspect of the present invention, the present invention provides methods of manufacturing of the compositions, formulations, blends or dosage forms of this invention, such as e.g. by using methods known to one skilled in the art and/or in a manner as described herein, for example they may be obtained by processes comprising using (e.g. mixing, combining, blending and/or composing) the components and/or ingredients, or pre-mixtures thereof, mentioned hereinbefore and hereinafter, as well as the present invention further provides compositions, formulations, blends or dosage forms obtainable by these methods or processes and/or obtainable from the components, ingredients, pre-mixtures and/or mixtures mentioned hereinbefore and hereinafter.

In a further aspect of the present invention, the present invention provides a pharmaceutical composition, formulation, blend or dosage form of this invention which is substantially free of or only marginally comprises impurities and/or degradation products; that means, for example, that the composition, formulation, blend or dosage from includes about <5%, or about <4%, or about <3%, or less than about 2%, preferably less than about 1%, more preferably less than about 0.5%, even more preferably less than about 0.2% of any individual or total impurity or degradation product(s) by total weight, such as e.g. N-acetyl and/or N-carbamoyl derivative of the free base type DPP-4 inhibitor. The content and/or degradation can be determined by well-known analytical methods, for example using HPLC methods.

In this context, in a further aspect of the present invention, the present invention provides derivatives of a DPP-4 inhibitor having an amino group, particularly a free primary amino group, as mentioned herein, said derivatives being obtainable by acetylation of the amino group (e.g. to yield the group-NHC(O)CH$_3$) or by carbamoylation of the amino group (e.g. to yield the group —NHC(O)NH$_2$).

Dosage forms for the FDC formulations of this invention:

Another purpose of this invention is to develop the FDC formulations of this invention with a reasonable tablet size, with good tablet properties (e.g. stability, hardness, friability, disintegration, content uniformity and the like) and, in a preferred embodiment, without disturbing the original dissolution profiles of each mono tablet in case of desired proof of bioequivalence with minimized risk of failure.

Designing of the dosage form is an important matter not only to optimize the tablet size and dissolution profiles but also to minimize the amount of stabilizing agent, because the pH change by dissolving of buffering agent may affect the dissolution profiles of the DPP-4 inhibitor or a partner drug. The selection of the dosage form is depending on the dose strengths of the active ingredients used and their physico-chemical and solid state characteristics.

A conventional approach (i.e. physical separation) may not be useful for stabilization of certain DPP-4 inhibitors of this invention. A buffering agent like L-arginine need to be added into the formulation for suppressing degradation, however it may be necessary to minimize the amount of L-arginine because its alkaline characteristics give a negative impact on the dissolution profiles or the stability of the DPP-4 inhibitor or a partner drug.

Thus, it has been found that suitable dosage forms for the FDC formulations of this invention are film-coated tablets (film-coating for drug loading, such as particularly DPP-4 inhibitor drug loading by film coating on tablet cores containing the partner drug), mono-layer tablets, bi-layer tablets, tri-layer tablets and press-coated tablets (e.g. tablet-in-tablet or bull's eye tablet with DPP-4 inhibitor core), which dosage forms are good measures to achieve the goal under consideration of desired pharmaceutical profiles and characteristics of a DPP-4 inhibitor and a partner drug used.

Said dosage forms have been found to be applicable to the FDC formulations either keeping the original dissolution profiles of each mono tablet or adjusting the profiles to desired levels, e.g. including extended release characteristics, and a reasonable tablet size.

A typical mono-layer tablet of this invention comprises a DPP-4 inhibitor, metformin hydrochloride, L-arginine, one or more fillers (such as e.g. corn starch), one or more binders (such as e.g. copovidone), one or more glidants (such as e.g. colloidal anhydrous silica) and one or more lubricants (such as e.g. magnesium stearate).

In a preferred embodiment of the present invention, the present invention is directed to an oral solid pharmaceutical composition, preferably a tablet, particularly a mono-layer tablet comprising or made from 1-[(4-methyl-quinazolin-2-yl)methyl]-3-methyl-7-(2-butyn-1-yl)-8-(3-(R)-amino-piperidin-1-yl)-xanthine (also known as BI 1356, e.g. in an amount of 2.5 mg), metformin (particularly metformin hydrochloride, e.g. in an amount of 500 mg, 850 mg or 1000 mg), L-arginine, and one or more pharmaceutical excipients, particularly one or more fillers (e.g. corn starch), one or more binders (e.g. copovidone), one or more glidants (e.g. colloidal anhydrous silica) and/or one or more lubricants (e.g. magnesium stearate), as well as, optionally, a film coat e.g. comprising one or more film-coating agents (e.g. hypromellose), one or more plasticizers (e.g. propylene glycol), one or more pigments (e.g. titanium dioxide, iron oxide red and/or iron oxide yellow) and/or one or more glidants (e.g. talc).

A method of manufacturing a tablet of this invention comprises tabletting (e.g. compression) of one or more final blends in form of granules. Granules of the (final) blend(s) according to this invention may be prepared by methods well-known to one skilled in the art (e.g. high shear wet granulation or fluid bed granulation). Granules according to this invention as well as details of granulation processes (including their separate steps) for the preparation of granules of this invention are described by way of example in the following examples.

An illustrative granulation process for the preparation of granules comprising the mono-layer composition comprises i.) combining (e.g. dissolving or dispersing) L-arginine, a binder (e.g. copovidone) and, optionally, the DPP-4 inhibitor (e.g. BI 1356) in a solvent or mixture of solvents such as purified water at ambient temperature to produce a granulation liquid;

ii.) blending metformin HCl, a filler (e.g. corn starch) and, optionally, the DPP-4 inhibitor (e.g. BI 1356) in a suitable mixer (e.g. fluid-bed granulator) to produce a pre-mix;

wherein the DPP-4 inhibitor (e.g. BI 1356) may be included either in the granulation liquid obtained in i.) or in the pre-mix obtained in ii.), preferably BI 1356 is dispersed in the granulation liquid and is absent in the pre-mix;

iii.) spraying the granulation-liquid into the pre-mix and granulating the mixture for example in a fluid-bed granulator, preferably under dry condition;

iv.) drying the granulate, e.g. at about 70° C. inlet air temperature until the desired loss on drying value in the range of 1-2% is obtained;

v.) delumping the dried granulate for example by sieving through a sieve with a mesh size of 0.5 to 1.0 mm;

vi.) blending the sieved granulate and preferably sieved glidant (e.g. colloidal anhydrous silica) in a suitable blender;

vii.) adding preferably sieved lubricant (e.g. magnesium stearate) to the granulate for final blending for example in the free-fall blender.

Preferentially, a mono-layer tablet according to this invention comprises or is obtainable from a mixture comprising any one of the following amounts (1), (2) or (3) of active ingredients and L-arginine:

(1) 2.5 mg of 1-[(4-methyl-quinazolin-2-yl)methyl]-3-methyl-7-(2-butyn-1-yl)-8-(3-(R)-amino-piperidin-1-yl)-xanthine free base, 500 mg metformin hydrochloride, and 12.5 mg L-arginine;

(2) 2.5 mg of 1-[(4-methyl-quinazolin-2-yl)methyl]-3-methyl-7-(2-butyn-1-yl)-8-(3-(R)-amino-piperidin-1-yl)-xanthine free base, 850 mg metformin hydrochloride, and 21.2 mg L-arginine;

(3) 2.5 mg of 1-[(4-methyl-quinazolin-2-yl)methyl]-3-methyl-7-(2-butyn-1-yl)-8-(3-(R)-amino-piperidin-1-yl)-xanthine free base, 1000 mg metformin hydrochloride, and 25 mg L-arginine.

A typical bi-layer tablet of this invention comprises a DPP-4 inhibitor portion comprising a DPP-4 inhibitor, L-arginine, one or more fillers (such as e.g. D-mannitol, pregelatinized starch and corn starch), one or more binders (such as e.g. copovidone) and one or more lubricants (such as e.g. magnesium stearate), and a metformin HCl portion comprising metformin hydrochloride, one or more fillers (such as e.g. corn starch), one or more binders (such as e.g. copovidone), one or more glidants (such as e.g. colloidal anhydrous silica) and one or more lubricants (such as e.g. magnesium stearate).

Preferentially, a bi-layer tablet according to this invention comprises or is obtainable from a mixture comprising any one of the following amounts (1), (2) or (3) of active ingredients and L-arginine:

(1) 2.5 mg of 1-[(4-methyl-quinazolin-2-yl)methyl]-3-methyl-7-(2-butyn-1-yl)-8-(3-(R)-amino-piperidin-1-yl)-xanthine free base, 500 mg metformin hydrochloride, and 2.5 mg L-arginine;

(2) 2.5 mg of 1-[(4-methyl-quinazolin-2-yl)methyl]-3-methyl-7-(2-butyn-1-yl)-8-(3-(R)-amino-piperidin-1-yl)-xanthine free base, 850 mg metformin hydrochloride, and 2.5 mg L-arginine;

(3) 2.5 mg of 1-[(4-methyl-quinazolin-2-yl)methyl]-3-methyl-7-(2-butyn-1-yl)-8-(3-(R)-amino-piperidin-1-yl)-xanthine free base, 1000 mg metformin hydrochloride, and 2.5 mg L-arginine.

A typical press-coated tablet (tablet-in-tablet or bull's eye tablet) of this invention comprises a DPP-4 inhibitor core portion comprising a DPP-4 inhibitor, L-arginine, one or more fillers (such as e.g.

D-mannitol, pregelatinized starch and corn starch), one or more binders (such as e.g. copovidone) and one or more lubricants (such as e.g. magnesium stearate), and a metformin HCl portion comprising metformin hydrochloride, one or more fillers (such as e.g. corn starch), one or more binders (such as e.g. copovidone), one or more glidants (such as e.g. colloidal anhydrous silica) and one or more lubricants (such as e.g. magnesium stearate).

Preferentially, a press-coated tablet (tablet-in-tablet or bull's eye tablet) according to this invention comprises or is obtainable from a mixture comprising any one of the following amounts (1), (2) or (3) of active ingredients and L-arginine:

(1) 2.5 mg of 1-[(4-methyl-quinazolin-2-yl)methyl]-3-methyl-7-(2-butyn-1-yl)-8-(3-(R)-amino-piperidin-1-yl)-xanthine free base, 500 mg metformin hydrochloride, and 1.0 mg L-arginine;

(2) 2.5 mg of 1-[(4-methyl-quinazolin-2-yl)methyl]-3-methyl-7-(2-butyn-1-yl)-8-(3-(R)-amino-piperidin-1-yl)-xanthine free base, 850 mg metformin hydrochloride, and 1.0 mg L-arginine;

(3) 2.5 mg of 1-[(4-methyl-quinazolin-2-yl)methyl]-3-methyl-7-(2-butyn-1-yl)-8-(3-(R)-amino-piperidin-1-yl)-xanthine free base, 1000 mg metformin hydrochloride, and 1.0 mg L-arginine.

A typical film-coated tablet (DPP-4 inhibitor coating on metformin HCl tablet, i.e. drug layering by film-coating for drug loading) of this invention comprises a metformin HCl core portion comprising metformin hydrochloride, one or more fillers (such as e.g. corn starch), one or more binders (such as e.g. copovidone), one or more glidants (such as e.g. colloidal anhydrous silica) and one or more lubricants (such as e.g. magnesium stearate), wherein said core portion is seal-coated with a film coat comprising one or more film-coating agents (such as e.g. hypromellose), one or more plasticizers (such as e.g. propylene glycol), one or more pigments (such as e.g. titanium dioxide, iron oxide red and/or iron oxide yellow) and one or more glidants (such as e.g. talc); and a DPP-4 inhibitor layer comprising a DPP-4 inhibitor, L-arginine, one or more film-coating agents (such as e.g. hypromellose) and one or more plasticizers (such as e.g. propylene glycol).

Preferentially, a film-coated tablet (DPP4-inhibitor drug loading) according to this invention comprises or is obtainable from a mixture comprising any one of the following amounts (1), (2) or (3) of active ingredients and L-arginine:

(1) 2.5 mg of 1-[(4-methyl-quinazolin-2-yl)methyl]-3-methyl-7-(2-butyn-1-yl)-8-(3-(R)-amino-piperidin-1-yl)-xanthine free base, 500 mg metformin hydrochloride, and 2.5 mg L-arginine;

(2) 2.5 mg of 1-[(4-methyl-quinazolin-2-yl)methyl]-3-methyl-7-(2-butyn-1-yl)-8-(3-(R)-amino-piperidin-1-yl)-xanthine free base, 850 mg metformin hydrochloride, and 2.5 mg L-arginine;

(3) 2.5 mg of 1-[(4-methyl-quinazolin-2-yl)methyl]-3-methyl-7-(2-butyn-1-yl)-8-(3-(R)-amino-piperidin-1-yl)-xanthine free base, 1000 mg metformin hydrochloride, and 2.5 mg L-arginine.

Preferably, these abovementioned tablets (mono-, bi-layer, press-coated and drug-coated tablets) are further over-coated with a final film coat, which comprises a film-coating agent (such as e.g. hypromellose), a plasticizer (such as e.g. propylene glycol), pigments (such as e.g. titanium dioxide, iron oxide red and/or iron oxide yellow) and a glidant (such as e.g. talc). Typically this additional film over-coat may represent 1-4%, preferentially 1-2%, of the total mass of the composition.

The following dosage forms of the invention can be applied to the FDC formulation of 1-[(4-methyl-quinazolin-2-yl)methyl]-3-methyl-7-(2-butyn-1-yl)-8-(3-(R)-amino-piperidin-1-yl)-xanthine free base (BI 1356) and metformin hydrochloride based on the characteristics of drug substances and requirements of the desired pharmaceutical profiles:

a) Mono-Layer Tablets

Mono-layer tablets with L-arginine show satisfactory stability results, good dissolution properties and good content uniformity (CU). Mono-layer tablets can be manufactured using conventional technologies (including fluid-bed granulation for the DPP-4 inhibitor and metformin hydrochloride, e.g. comprising adding the DPP-4 inhibitor as powder or as an aqueous suspension in the granulation liquid to the fluid bed granulator).

b) Bi-Layer Tablets

Bi-layer tablets with L-arginine show promising stability results, good dissolution properties and good CU. Bi-layer tablets can be manufactured using conventional bi-layer tableting technologies (e.g. rotary bi-layer tableting machine).

c) Press-Coated Tablets

Press-coated tablets (tablet-in-tablets and advanced press-coated bull's eye tablets) show promising stability, good CU and dissolution. Press-coated tablets can be manufactured using conventional press-coating technology, such as e.g. on a Kilian tablet press to obtain tablet-in-tablet or on other conventional press-coater to obtain bull's eye tablet. As an advantage of this approach, it is easy to minimize the amount of L-arginine in the formulation and control the assay and CU of the DPP-4 inhibitor portion (very small amount of drug loading; 2.5 mg/tablet where the dose strengths of metformin HCl are 500, 850 and 1000 mg/tablet). Another advantage is that DPP-4 inhibitor- and metformin HCl-portion can be designed flexibly to minimize the tablet size. A modified press-coated tablet named "bull's eye tablet" may be a universal dosage potentially for bi-layer tablets as well as other FDC. Bull's eye tablet can be manufactured in a one-step press-coating without separate core formation (like in bi-layer tableting) being necessary.

It is to be noted that within the meaning of this invention the skilled person is aware about what is meant with the phrase "bull's eye tablet" used herein. As it known to the skilled person, this tablet (also referred to as an inlay tablet or a dot) is composed of an outer coat and an inner core, and in which, instead of the inner core zone being completely surrounded by the outer coat, one surface of the zone corresponding to the inner core zone is exposed.

d) Film-Coated Tablets (Drug Layering by Film-Coating for Drug Loading)

Coating of DPP-4 inhibitor drug substance on the metformin HCl tablets shows acceptable dissolution results and promising stability data. L-arginine needs to be added into film-coating for stabilization. As an advantage for this approach, it is possible to integrate DPP-4 inhibitor portion into a partner drug portion as it is, even if the dosage form is a modified/controlled release formulation. Within the film-coating process coating endpoint determination is necessary via analytics.

The method of layering of the DPP-4 inhibitor by film-coating as described herein (including the steps of seal-coating, drug-loading and, optional, over-coating) may be applied to any kind of cores or tablets which may comprise an active ingredient (e.g. a partner drug as mentioned herein), for example metformin cores or tablets, such as e.g. immediate release metformin tablets, sustained release metformin tablets, extended release metformin tablets, modified release metformin tablets, controlled release metformin tablets or delayed release metformin tablets. Thus, the present invention further relates to a tablet which comprises a film-coat layer comprising the DPP-4 inhibitor, a film-forming agent (e.g. hypromellose), a plasticizer (e.g. propylene glycol) and L-arginine, or which is obtainable by comprising using such a method of layering of the DPP-4 inhibitor by film-coating as described herein. The present invention also relates to a FDC tablet comprising an immediate or extended release metformin tablet core, a seal coat, a film-coat layer comprising the DPP-4 inhibitor, and, optionally, an over-coat; e.g. each as described herein, as well as to such a FDC tablet made by a process comprising the following steps of seal-coating on a metformin tablet core, layering of a DPP-4 inhibitor by film-coating and, optional, over-coating, e.g. each step such as described herein.

Pharmaceutical immediate release dosage forms of this invention preferably have dissolution properties such that after 45 minutes for each of the active ingredients at least 75%, even more preferably at least 90% by weight of the respective active ingredient is dissolved. In a particular embodiment, after 30 minutes for each of the active ingredients especially of the mono-layer tablet according to this invention (including tablet core and film-coated tablet) at least 70-75% (preferably at least 80%) by weight of the respective active ingredient is dissolved. In a further embodiment, after 15 minutes for each of the active ingredients especially of the mono-layer tablet according to this invention (including tablet core and film-coated tablet) at least 55-60% by weight of the respective active ingredient is dissolved. The dissolution properties can be determined in standard dissolution tests, e.g. according to standard pharmacopeias (e.g. using paddle method with agitation speed of 50 rpm, 0.1M hydrochloric acid as dissolution medium at a temperature of 37° C., and HPLC (BI 1356) and UV (metformin) analysis of the samples).

In the pharmaceutical compositions and pharmaceutical dosage forms according to the invention BI 1356, for example a crystalline form thereof, preferably has a particle size distribution (preferably by volume) such that at least 90% of the respective active pharmaceutical ingredient has a particle size smaller than 200 $\mu$m, i.e. X90<200 $\mu$m, more preferably X90≤150 $\mu$m. More preferably the particle size distribution is such that X90≤100 $\mu$m, even more preferably X90≤75 $\mu$m. In addition the particle size distribution is preferably such that X90>0.1 $\mu$m, more preferably X90≥1 $\mu$m, most preferably X90≥5 $\mu$m. Therefore preferred particle size distributions are such that 0.1 $\mu$m<X90<200 $\mu$m, particularly 0.1 $\mu$m<X90≤150 $\mu$m, more preferably 1 $\mu$m≤X90≤150 $\mu$m, even more preferably 5 $\mu$m≤X90≤100 $\mu$m. A preferred example of a particle size distribution of BI 1356 is such that X90≤50 $\mu$m or 10 $\mu$m≤X90≤50 $\mu$m. It can be found that a pharmaceutical composition comprising BI 1356 with a particle size distribution as indicated hereinbefore shows desired properties (e.g. with regard to dissolution, content uniformity, production, or the like). The indicated particle size properties are determined by laser-diffraction method, in particular low angle laser light scattering, i.e. Fraunhofer diffraction. Alternatively, the particle size properties can be also determined by microscopy (e.g. electron microscopy or scanning electron microscopy).

The results of the particle size distribution determined by different techniques can be correlated with one another.

Optimized Formulation of Metformin HCl Portion:

Another purpose of this invention is to provide improved formulations of the metformin HCl portion of the pharmaceutical compositions according to this invention.

For the metformin HCl part a high drug load is advantageous to be achieved as a pre-requisite for a reasonable small tablet size.

Thus, it has been found that drug load of metformin HCl and compactability (compression force-crushing strength profile) of the tablets of this invention can be improved by surface treatment of metformin HCl with a water-soluble polymer, particularly copolyvidone.

Several water-soluble polymers including polyvinyl alcohol (PVA), hypromellose (HPMC), hydroxypropyl cellulose (HPC), methyl cellulose (MC), Povidone (PVP) and copolyvidone may be tested to improve compactability (compression force-crushing strength profile). As the results, PVA shows the best effect in terms of compactability but the manufacturability can be poor due to sticking problem during fluid-bed granulation. Further on, PVA may be not finally selected because of its negative impact on the stability of certain DPP-4 inhibitors of this invention.

metformin HCl needs to be conducted before starting of granulation with the DPP-4 inhibitor. The heating/drying at 80° C. with a fluid-bed granulator may be helpful to reduce an excessive amount of volatile impurities (which might be urea) in the metformin HCl.

The present invention is not to be limited in scope by the specific embodiments described herein. Various modifications of the invention in addition to those described herein may become apparent to those skilled in the art from the present disclosure. Such modifications are intended to fall within the scope of the appended claims.

All patent applications cited herein are hereby incorporated by reference in their entireties.

Further embodiments, features and advantages of the present invention may become apparent from the following examples. The following examples serve to illustrate, by way of example, the principles of the invention without restricting it.

EXAMPLES

1. Mono-Layer Tablet

The composition of mono-layer tablets for a DPP-4 inhibitor of this invention (BI 1356)+metformin HCl FDC (Film-coated Tablets) is shown in Table 1.

TABLE 1

Composition of BI 1356 + Metformin HCl FDC Mono-layer Tablets

| Ingredient | Dose Strength (BI 1356/metformin HCl), mg | | | | | |
| | 2.5/500 | | 2.5/850 | | 2.5/1000 | |
| | [mg] | [%] | [mg] | [%] | [mg] | [%] |
|---|---|---|---|---|---|---|
| BI 1356 | 2.50 | 0.42 | 2.50 | 0.25 | 2.50 | 0.21 |
| Metformin Hydrochloride | 500.0 | 84.75 | 850.00 | 85.00 | 1000.00 | 84.75 |
| L-Arginine | 12.50 | 2.12 | 21.20 | 2.12 | 25.00 | 2.12 |
| Corn starch | 20.00 | 3.39 | 33.10 | 3.31 | 42.50 | 3.60 |
| Copovidone | 47.50 | 8.05 | 80.50 | 8.05 | 95.00 | 8.05 |
| Colloidal Anhydrous Silica | 2.50 | 0.42 | 4.20 | 0.42 | 5.00 | 0.42 |
| Magnesium stearate | 5.00 | 0.85 | 8.50 | 0.85 | 10.00 | 0.85 |
| Purified water* | 186** | | 315** | | 372** | |
| | | | | | | |
| Total Mass (tablet core) | 590.00 | 100.00 | 1000.00 | 100.00 | 1180.00 | 100.00 |
| Hypromellose (5 mPa*s) | 6.00 | 50.00 | 8.00 | 50.00 | 9.00 | 50.00 |
| Propylene glycol | 0.60 | 5.00 | 0.80 | 5.00 | 0.90 | 5.00 |
| Talc | 2.88 | 18.50 | 2.96 | 18.50 | 4.455 | 18.50 |
| Titanium dioxide | 2.40 | 25.00 | 4.00 | 25.00 | 3.60 | 25.00 |
| Iron oxide, yellow | 0.12 | 1.25 | 0.20 | 1.25 | | |
| Iron oxide, red | | | 0.04 | 0.25 | 0.045 | 1.25 |
| Purified water** | 88** | | 117** | | 132** | |
| | | | | | | |
| Total Mass (film-coat) | 12.00 | 100.00 | 16.00 | 100.00 | 18.00 | 100.00 |
| | | | | | | |
| Total Mass (coated tablet) | 602.00 | | 1016.00 | | 1198.00 | |

**Removed during processing, does not appear in final product

Formulation optimization studies have identified a composition with over 84% drug load of metformin HCl and improved crushing strength by surface-treatment of metformin HCl with the water-soluble polymer copolyvidone.

Therefore, finally, copolyvidone is selected and the amount can be optimized, advantageously resulting in stable formulations and the viscosity of the granulating solution is enough low to prepare the aqueous solution and operate spraying by a fluid-bed granulator.

In optional addition, it has been found that heating/drying of metformin HCl drug substance is effective to improve the stability of certain DPP-4 inhibitors of this invention in combination with metformin HCl. The pre-treatment for Manufacturing Procedure (Mono-Layer Tablets):

DPP-4 inhibitor of this invention (e.g. BI 1356)+metformin HCl FDC mono-layer tablets are produced by a fluid-bed granulation process and a conventional tableting process with a rotary press. Optionally, metformin HCl and corn starch may be pre-treated by heating in a chamber of fluid-bed granulator to remove excessive HCl and/or impurity products before mixing with the active DPP-4 inhibitor ingredient. After the optional pre-treatment of metformin HCl and corn starch, the DPP-4 inhibitor is either added as powder and premixed before fluid-bed granulation is conducted by spraying of "Granulation Liquid" composed of copolyvidon (Kollidon VA64), L-arginine and purified water, or directly dispersed in the "granulation liquid". After finishing of fluid-bed granulation, the granulate is sieved with a suitable screen. The sieved granulate is blended with colloidal anhydrous silica (Aerosil 200) and magnesium stearate as a lubricant. The final mixture is compressed into tablets using a conventional rotary tablet press.

The tablet cores may be film-coated by an aqueous film-coating suspension, containing hypromellose as film-forming agent, propylene glycol as plasticizer, talc as glidant and the pigments yellow iron oxide and/or red iron oxide and titanium dioxide.

Narrative more specific description of the preferred manufacturing process for the mono-layer tablets:

a) Metformin HCl and corn starch are sieved using a screen with a mesh size of 0.5 to 1 mm before dispensing.

b) L-arginine, BI 1356 and finally copolyvidon are dissolved resp. dispersed in purified water at ambient temperature with a propeller mixer to produce the "Granulation Liquid".

c) Metformin HCl and corn starch are sucked into a chamber of a suitable fluid-bed granulator and pre-heated up to a product temperature target of approx. 36° C.

d) Immediately after the product temperature target is reached, the "Granulation Liquid" is sprayed into the mixture for fluid-bed granulating under dry condition to avoid blocking during granulation.

e) At the end of spraying, the resultant granulate is dried at approx. 70 C inlet air temperature until the desired LOD value (i.e. 1-2%) is reached.

f) The granulate is sieved using a screen with a mesh size of 0.5 to 1.0 mm.

g) The sieved granulate and colloidal anhydrous silica (Aerosil 200) are blended with a suitable blender. Aerosil 200 should be pre-sieved with a small portion of the sieved granulate through a 0.8 mm-screen before use.

h) Magnesium stearate is passed through a 0.8 mm sieve and added into the granulate. Subsequently the "Final Blend" is produced by final blending in the free-fall blender.

i) The "Final Blend" is compressed into tablets with a rotary press.

j) Titanium dioxide, propylene glycol and iron oxide (yellow, red or yellow and red) are dispersed in purified water with a high shear homo-mixer. Then, hypromellose and talc are added and dispersed with a homo-mixer and propeller mixer at ambient temperature to produce the "Coating Suspension".

k) The tablet cores are coated with the "Coating Suspension" to the target weight gain to produce the "Film-coated Tablets". The "Coating Suspension" should be stirred again before use and kept stirring slowly during the coating (spraying) process.

Narrative more specific description of an alternative manufacturing process for the mono-layer tablets:

a) Metformin HCl is sieved using a screen with a mesh size of 0.5 to 1 mm before weighing.

b) L-arginine and copolyvidon are dissolved in purified water at ambient temperature with a propeller mixer to produce the "Granulation Liquid"

c) Metformin HCl and corn starch are heated in a chamber of fluid-bed granulator at 70-80° C. for more than 15 min until the product temperature reaches 60° C.

d) BI 1356 is added into the container, then blended with metformin HCl and corn starch in the fluid-bed granulator.

e) The "Granulation Liquid" is sprayed into the mixture for fluid-bed granulating under dry condition to avoid blocking during granulation.

f) At the end of spraying, the resultant granulate is dried at 70-80° C. until the desired LOD value (i.e. 1-2%), in case the LOD is more than 2%.

g) The granulate is sieved using a screen with a mesh size of 0.5 to 1.0 mm.

h) The sieved granulate and colloidal anhydrous silica (Aerosil 200) are blended with a suitable blender. Aerosil 200 should be sieved with a 0.5 mm-screen before use.

i) Magnesium stearate passed through a 0.5 mm sieve and added into the granulate. Subsequently the "Final Blend" is produced by final blending in the blender.

j) The "Final Blend" is compressed into tablets with a rotary press.

k) Hypromellose and propylene glycol are dissolved in purified water with a propeller mixer. Talc, titanium dioxide, and iron oxide (yellow, or yellow and red) are dispersed in purified water with a homo-mixer. The suspension is added into the hypromellose solution, then mixed with a propeller mixer at ambient temperature to produce the "Coating Suspension".

l) The tablet cores are coated with the "Coating Suspension" to the target weight gain to produce the "Film-coated Tablets". The "Coating Suspension" should be stirred again before use and kept stirring slowly during the coating (spraying) process.

2. Bi-Layer Tablet

The composition of bi-layer tablets for a DPP-4 inhibitor of this invention (BI 1356)+metformin HCl FDC (Film-coated Tablets) is shown in Table 2.

TABLE 2

| Composition of BI 1356 + Metformin HCl FDC Bi-layer Tablets | | | | | | |
|---|---|---|---|---|---|---|
| | Dose Strength (BI 1356/metformin HCl), mg | | | | | |
| | 2.5/500 | | 2.5/850 | | 2.5/1000 | |
| Ingredient | [mg] | [%] | [mg] | [%] | [mg] | [%] |
| BI 1356-portion: | (450) | (100) | (450) | (100) | (450) | (100) |
| BI 1356 | 2.50 | 0.556 | 2.50 | 0.556 | 2.50 | 0.556 |
| L-Arginine | 2.50 | 0.556 | 2.50 | 0.556 | 2.50 | 0.556 |
| D-mannitol | 334.75 | 74.39 | 334.75 | 74.39 | 334.75 | 74.39 |
| Pregelatinized starch | 45.00 | 10.00 | 45.00 | 10.00 | 45.00 | 10.00 |
| Corn starch | 45.00 | 10.00 | 45.00 | 10.00 | 45.00 | 10.00 |

TABLE 2-continued

Composition of BI 1356 + Metformin HCl FDC Bi-layer Tablets

| | Dose Strength (BI 1356/metformin HCl), mg | | | | | |
| | 2.5/500 | | 2.5/850 | | 2.5/1000 | |
| Ingredient | [mg] | [%] | [mg] | [%] | [mg] | [%] |
|---|---|---|---|---|---|---|
| Copovidone | 13.50 | 3.00 | 13.50 | 3.00 | 13.50 | 3.00 |
| Magnesium stearate | 6.75 | 1.50 | 6.75 | 1.50 | 6.75 | 1.50 |
| Metformin HCl-portion: | (570) | (100) | (969) | (100) | (1140) | (100) |
| Metformin Hydrochloride | 500.0 | 87.72 | 850.00 | 87.72 | 1000.00 | 87.72 |
| Corn starch | 15.00 | 2.63 | 25.50 | 2.63 | 30.00 | 2.63 |
| Copovidone | 47.50 | 8.33 | 80.57 | 8.33 | 95.00 | 8.33 |
| Colloidal Anhydrous Silica | 2.50 | 0.44 | 4.25 | 0.44 | 5.00 | 0.44 |
| Magnesium stearate | 5.00 | 0.88 | 8.50 | 0.88 | 10.00 | 0.88 |
| Total Mass (tablet core) | 1020 | 100.00 | 1419 | 100.00 | 1590 | 100.00 |
| Hypromellose (5 mPa*s) | 8.00 | 50.00 | 9.50 | 50.00 | 11.00 | 50.00 |
| Propylene glycol | 0.80 | 5.00 | 0.95 | 5.00 | 1.10 | 5.00 |
| Talc | 2.96 | 18.50 | 3.515 | 18.50 | 4.07 | 18.50 |
| Titanium dioxide | 4.00 | 25.00 | 4.75 | 25.00 | 5.50 | 25.00 |
| Iron oxide, yellow | 0.20 | 1.25 | 0.2375 | 1.25 | 0.275 | 1.25 |
| Iron oxide, red | 0.04 | 0.25 | 0.0475 | 0.25 | 0.055 | 0.25 |
| Total Mass (film-coat) | 16.00 | 100.00 | 19.00 | 100.00 | 22.00 | 100.00 |
| Total Mass (coated tablet) | 1036 | 100.00 | 1438 | 100.00 | 1612 | 100.00 |

Manufacturing Procedure (Bi-Layer Tablets):

DPP-4 inhibitor of this invention (e.g. BI 1356)+metformin HCl FDC bi-layer tablets are produced by a high-shear wet granulation process (for DPP-4 inhibitor-granulate), a fluid-bed granulation process (for metformin HCl-granulate), and bi-layer tableting process with a multi-layer rotary press.

DPP-4 inhibitor-granulate: By using a high-shear granulator the active DPP-4 inhibitor ingredient is pre-mixed with the diluents D-mannitol and pregelatinized starch. The mixture is moistened with granulating liquid, containing purified water and copovidone as a binder. After further mixing, drying and sieving, the dried granulate is blended with magnesium stearate as a lubricant.

Narrative more specific description of the manufacturing process for the BI 1356-granulate:

a. Copovidone and L-arginine are dissolved in purified water at ambient temperature to produce the Granulation Liquid.

b. BI 1356, mannitol and pregelatinized starch are blended in a suitable mixer, to produce the Pre-Mix.

c. The Pre-mix is moistened with the Granulation Liquid and subsequently granulated.

d. The moist granulate is sieved through a suitable sieve.

e. The granulate is dried at about 50° C. (maximum 60° C.) in a suitable dryer until the desired loss on drying value is obtained.

f. The dried granulate is sieved through a sieve with a mesh size of 1.0 mm.

g. Magnesium stearate is passed through a 1.0 mm sieve and added to the granulate. Subsequently the "Final Blend A" is produced by final blending in a suitable blender.

Metformin HCl-granulate: Metformin HCl and corn starch are pre-treated by heating in a chamber of fluid-bed granulator to remove excessive HCl and/or impurity products. After the pre-treatment of metformin HCl and corn starch, fluid-bed granulation is conducted by spraying of "Granulation Liquid" composed of copolyvidon (Kollidon VA64) and purified water. After finishing of fluid-bed granu-lation, the granulate is sieved with a suitable screen. The sieved granulate is blended with colloidal anhydrous silica (Aerosil 200) and magnesium stearate as a lubricant.

Narrative More Specific Description of the Manufacturing Process for the Metformin HCl-Granulate:

a) Metformin HCl is sieved using a screen with a mesh size of 0.5 to 1 mm before weighing.

b) Copolyvidon is dissolved in purified water at ambient temperature with a propeller mixer to produce the "Granulation Liquid"

c) Metformin HCl and corn starch are heated in a chamber of fluid-bed granulator at 70-80° C. for more than 15 min until the product temperature reaches 60° C.

d) The "Granulation Liquid" is sprayed into the mixture for fluid-bed granulating under dry condition to avoid blocking during granulation.

e) At the end of spraying, the resultant granulate is dried at 70-80° C. until the desired LOD value (i.e. 1-2%), in case the LOD is more than 2%.

f) The granulate is sieved using a screen with a mesh size of 0.5 to 1.0 mm.

g) The sieved granulate and colloidal anhydrous silica (Aerosil 200) are blended with a suitable blender. Aerosil 200 should be sieved with a 0.5 mm-screen before use.

h) Magnesium stearate passed through a 0.5 mm sieve and added into the granulate. Subsequently the "Final Blend B" is produced by final blending in the blender.

The "Final Blend A" and "Final Blend B" are compressed into bi-layer tablets using a multi-layer rotary press. The tablet cores may be film-coated by an aqueous film-coating suspension, containing hypromellose as film-forming agent, propylene glycol as plasticizer, talc as glidant and the pigments yellow iron oxide and/or red iron oxide and titanium dioxide.

Narrative More Specific Description of the Manufacturing Process for the Film-Coating:

a) Hypromellose and propylene glycol are dissolved in purified water with a propeller mixer. Talc, titanium dioxide, and iron oxide (yellow, red or yellow and red) are dispersed in purified water with a homo-mixer. The suspension is added into the hypromellose solution, then mixed with a propeller mixer at ambient temperature to produce the "Coating Suspension".

b) The tablet cores are coated with the "Coating Suspension" to the target weight gain to produce the "Film-coated Tablets". The "Coating Suspension" should be stirred again before use and kept stirring slowly during the coating (spraying) process.

3. Tablet-in-Tablet or Bull's Eye Tablet

The composition of Tablet-in-Tablet or Bull's eye tablets for a DPP-4 inhibitor of this invention (BI 1356)+metformin HCl FDC (Film-coated Tablets) is shown in Table 3.

Narrative More Specific Description of the Manufacturing Process for the BI 1356 Core-Tablets:

a. Copovidone and L-arginine are dissolved in purified water at ambient temperature to produce the Granulation Liquid.

b. BI 1356, mannitol and pregelatinized starch are blended in a suitable mixer, to produce the Pre-Mix.

c. The Pre-mix is moistened with the Granulation Liquid and subsequently granulated.

d. The moist granulate is sieved through a suitable sieve.

e. The granulate is dried at about 50° C. (maximum 60° C.) in a suitable dryer until the desired loss on drying value is obtained.

f. The dried granulate is sieved through a sieve with a mesh size of 1.0 mm.

TABLE 3

Composition of BI 1356 + Metformin HCl
FDC Tablet-in-Tablet or Bull's Eye Tablets

| | Dose Strength (BI 1356/metformin HCl), mg | | | | | |
| | 2.5/500 | | 2.5/850 | | 2.5/1000 | |
| Ingredient | [mg] | [%] | [mg] | [%] | [mg] | [%] |
|---|---|---|---|---|---|---|
| BI 1356-portion: | (45) | (100) | (45) | (100) | (45) | (100) |
| BI 1356 | 2.50 | 5.56 | 2.50 | 5.56 | 2.50 | 5.56 |
| L-Arginine | 1.00 | 2.22 | 1.00 | 2.22 | 1.00 | 2.22 |
| D-mannitol | 30.475 | 67.72 | 30.475 | 67.72 | 30.475 | 67.72 |
| Pregelatinized starch | 4.50 | 10.00 | 4.50 | 10.00 | 4.50 | 10.00 |
| Corn starch | 4.50 | 10.00 | 4.50 | 10.00 | 4.50 | 10.00 |
| Copovidone | 1.350 | 3.00 | 1.350 | 3.00 | 1.35 | 3.00 |
| Magnesium stearate | 0.675 | 1.50 | 0.675 | 1.50 | 6.75 | 1.50 |
| Metformin HCl-portion: | (570) | (100) | (969) | (100) | (1140) | (100) |
| Metformin Hydrochloride | 500.0 | 87.72 | 850.00 | 87.72 | 1000.00 | 87.72 |
| Corn starch | 15.00 | 2.63 | 25.50 | 2.63 | 30.00 | 2.63 |
| Copovidone | 47.50 | 8.33 | 80.57 | 8.33 | 95.00 | 8.33 |
| Colloidal Anhydrous Silica | 2.50 | 0.44 | 4.25 | 0.44 | 5.00 | 0.44 |
| Magnesium stearate | 5.00 | 0.88 | 8.50 | 0.88 | 10.00 | 0.88 |
| Total Mass (tablet core) | 615 | 100.00 | 1014 | 100.00 | 1185 | 100.00 |
| Hypromellose (5 mPa*s) | 6.00 | 50.00 | 8.00 | 50.00 | 9.00 | 50.00 |
| Propylene glycol | 0.60 | 5.00 | 0.80 | 5.00 | 0.90 | 5.00 |
| Talc | 2.22 | 18.50 | 2.96 | 18.50 | 3.33 | 18.50 |
| Titanium dioxide | 3.00 | 25.00 | 4.00 | 25.00 | 4.50 | 25.00 |
| Iron oxide, yellow | 0.15 | 1.25 | 0.20 | 1.25 | 0.225 | 1.25 |
| Iron oxide, red | 0.03 | 0.25 | 0.04 | 0.25 | 0.045 | 0.25 |
| Total Mass (film-coat) | 12.00 | 100.00 | 16.00 | 100.00 | 18.00 | 100.00 |
| Total Mass (coated tablet) | 627 | 100.00 | 1030 | 100.00 | 1203 | 100.00 |

Manufacturing Procedure (Tablet-In-Tablet or Bull's Eye Tablet):

DPP-4 inhibitor of this invention (e.g. BI 1356)+metformin HCl FDC Tablet-in-Tablet or Bull's eye tablets are produced by a high-shear wet granulation process (for DPP-4 inhibitor-granulate), a rotary press (for DPP-4 inhibitor core-tablet), a fluid-bed granulation process (for metformin HCl-granulate), and press-coating process with a press-coater.

DPP-4 inhibitor core-tablet: By using a high-shear granulator the active DPP-4 inhibitor ingredient is pre-mixed with the diluents D-mannitol and pregelatinized starch. The mixture is moistened with granulating liquid, containing purified water and copovidone as a binder. After further mixing, drying and sieving, the dried granulate is blended with magnesium stearate as a lubricant.

g. Magnesium stearate is passed through a 1.0 mm sieve and added to the granulate. Subsequently the "Final Blend" is produced by final blending in a suitable blender.

h. "Final Blend" is compressed into "BI 1356 core-tablets" with a rotary press.

Metformin HCl-granulate: Metformin HCl and corn starch are pre-treated by heating in a chamber of fluid-bed granulator to remove excessive HCl and/or impurity products. After the pre-treatment of metformin HCl and corn starch, fluid-bed granulation is conducted by spraying of "Granulation Liquid" composed of copolyvidon (Kollidon VA64) and purified water. After finishing of fluid-bed granulation, the granulate is sieved with a suitable screen. The sieved granulate is blended with colloidal anhydrous silica (Aerosil 200) and magnesium stearate as a lubricant.

Narrative More Specific Description of the Manufacturing Process for the Metformin HCl-Granulate:

a) Metformin HCl is sieved using a screen with a mesh size of 0.5 to 1 mm before weighing.

b) Copolyvidon is dissolved in purified water at ambient temperature with a propeller mixer to produce the "Granulation Liquid"

c) Metformin HCl and corn starch are heated in a chamber of fluid-bed granulator at 70-80° C. for more than 15 min until the product temperature reaches 60° C.

d) The "Granulation Liquid" is sprayed into the mixture for fluid-bed granulating under dry condition to avoid blocking during granulation.

e) At the end of spraying, the resultant granulate is dried at 70-80° C. until the desired LOD value (i.e. 1-2%), in case the LOD is more than 2%.

f) The granulate is sieved using a screen with a mesh size of 0.5 to 1.0 mm.

g) The sieved granulate and colloidal anhydrous silica (Aerosil 200) are blended with a suitable blender. Aerosil 200 should be sieved with a 0.5 mm-screen before use.

h) Magnesium stearate passed through a 0.5 mm sieve and added into the granulate. Subsequently "Metformin HCl-granulate" (Final Blend) is produced by final blending in the blender.

The "DPP-4 inhibitor core-tablets" and "Metformin HCl-granulate" are compressed into Tablet-in-Tablet or Bull's eye tablets using a press-coater. The difference between the Tablet-in-Tablet and Bull's eye tablet is the position of the core tablet.

Narrative More Specific Description of the Manufacturing Process for the Tablet-In-Tablet:

a) Fill a half of Metformin HCl-granulate in a die.

b) Place a BI 1356 core-tablet on the surface of Metformin HCl-granulate.

c) Cover the core-tablet with second half of Metformin HCl-granulate, then compressed into the tablet (Tablet-in-Tablet).

Narrative More Specific Description of the Manufacturing Process for the Bull's Eye Tablets:

a) Fill Metformin HCl-granulate in a die.

b) Place the BI 1356 core-tablet on the Metformin HCl-granulate in the die, then compressed into the tablet (Bull's eye tablet).

The tablets may be film-coated by an aqueous film-coating suspension, containing hypromellose as film-forming agent, propylene glycol as plasticizer, talc as glidant and the pigments yellow iron oxide and/or red iron oxide and titanium dioxide.

Narrative More Specific Description of the Manufacturing Process for the Film-Coating:

a) Hypromellose and propylene glycol are dissolved in purified water with a propeller mixer. Talc, titanium dioxide, and iron oxide (yellow, red or yellow and red) are dispersed in purified water with a homo-mixer. The suspension is added into the hypromellose solution, then mixed with a propeller mixer at ambient temperature to produce the "Coating Suspension".

b) The tablet cores are coated with the "Coating Suspension" to the target weight gain to produce the "Film-coated Tablets". The "Coating Suspension" should be stirred again before use and kept stirring slowly during the coating (spraying) process.

4. DPP-4 Inhibitor—Drug Layering on Metformin HCl Tablet (Film-Coating for Drug-Loading)

The composition of a DPP-4 inhibitor of this invention (BI 1356)+metformin HCl FDC (Film-coated Tablets) which are prepared by drug loading by film-coating on the Metformin HCl Tablet is shown in Table 4.

TABLE 4

Composition of BI 1356 + Metformin HCl FDC BI 1356-Coating on Metformin HCl Tablet

| | Dose Strength (BI 1356/metformin HCl), mg | | | | | |
| | 2.5/500 | | 2.5/850 | | 2.5/1000 | |
| Ingredient | [mg] | [%] | [mg] | [%] | [mg] | [%] |
|---|---|---|---|---|---|---|
| Metformin HCl-portion: | (570) | (100) | (969) | (100) | (1140) | (100) |
| Metformin Hydrochloride | 500.0 | 87.72 | 850.0 | 87.72 | 1000.0 | 87.72 |
| Corn starch | 15.0 | 2.63 | 25.5 | 2.63 | 30.0 | 2.63 |
| Copovidone | 47.5 | 8.33 | 80.57 | 8.33 | 95.0 | 8.33 |
| Colloidal Anhydrous Silica | 2.5 | 0.44 | 4.25 | 0.44 | 5.0 | 0.44 |
| Magnesium stearate | 5.0 | 0.88 | 8.5 | 0.88 | 10.0 | 0.88 |
| Total Mass (tablet core) | 570 | 100.00 | 969 | 100.00 | 1140 | 100.00 |
| Seal-coat (seal-coating): | (12) | (100) | (16) | (100) | (18) | (100) |
| Hypromellose (5 mPa*s) | 6.00 | 50.00 | 8.00 | 50.00 | 9.00 | 50.00 |
| Propylene glycol | 0.60 | 5.00 | 0.80 | 5.00 | 0.90 | 5.00 |
| Talc | 2.22 | 18.50 | 2.96 | 18.50 | 3.33 | 18.50 |
| Titanium dioxide | 3.00 | 25.00 | 4.00 | 25.00 | 4.50 | 25.00 |
| Iron oxide, yellow | 0.15 | 1.25 | 0.20 | 1.25 | 0.225 | 1.25 |
| Iron oxide, red | 0.03 | 0.25 | 0.04 | 0.25 | 0.045 | 0.25 |
| Drug-layer (drug-loading): | (25) | (100) | (25) | (100) | (25) | (100) |
| BI 1356 | 2.50 | 10.00 | 2.50 | 10.00 | 2.50 | 10.00 |
| L-Arginine | 2.50 | 10.00 | 2.50 | 10.00 | 2.50 | 10.00 |
| Hypromellose (5 mPa*s) | 18.00 | 72.00 | 18.00 | 72.00 | 18.00 | 72.00 |
| Propylene glycol | 2.00 | 8.00 | 2.00 | 8.00 | 2.00 | 8.00 |
| Over-coat (over-coating): | (12) | (100) | (16) | (100) | (18) | (100) |
| Hypromellose (5 mPa*s) | 6.00 | 50.00 | 8.00 | 50.00 | 9.00 | 50.00 |
| Propylene glycol | 0.60 | 5.00 | 0.80 | 5.00 | 0.90 | 5.00 |

TABLE 4-continued

Composition of BI 1356 + Metformin HCl FDC BI 1356-Coating on Metformin HCl Tablet

| | Dose Strength (BI 1356/metformin HCl), mg | | | | | |
| | 2.5/500 | | 2.5/850 | | 2.5/1000 | |
| Ingredient | [mg] | [%] | [mg] | [%] | [mg] | [%] |
|---|---|---|---|---|---|---|
| Talc | 2.22 | 18.50 | 2.96 | 18.50 | 3.33 | 18.50 |
| Titanium dioxide | 3.00 | 25.00 | 4.00 | 25.00 | 4.50 | 25.00 |
| Iron oxide, yellow | 0.15 | 1.25 | 0.20 | 1.25 | 0.225 | 1.25 |
| Iron oxide, red | 0.03 | 0.25 | 0.04 | 0.25 | 0.045 | 0.25 |
| Total Mass (film-coat) | 49 | 100.00 | 57 | 100.00 | 61 | 100.00 |
| Total Mass (coated tablet) | 619 | 100.00 | 1026 | 100.00 | 1201 | 100.00 |

Manufacturing Procedure (DPP-4 Inhibitor-Drug Layering by Film-Coating on Metformin HCl Tablet):

DPP-4 inhibitor (e.g. BI 1356)+metformin HCl FDC with drug coating is produced by a fluid-bed granulation process, a conventional tableting process, and film-coating process with three steps: seal-coating, drug-loading and over-coating. The over-coating may be able to be skipped by combining with the drug-loading, if the stability is acceptable.

Metformin HCl Tablets: Metformin HCl and corn starch are pre-treated by heating in a chamber of fluid-bed granulator to remove excessive HCl and/or impurity products. After the pre-treatment of metformin HCl and corn starch, fluid-bed granulation is conducted by spraying of "Granulation Liquid" composed of copolyvidon (Kollidon VA64) and purified water. After finishing of fluid-bed granulation, the granulate is sieved with a suitable screen. The sieved granulate is blended with colloidal anhydrous silica (Aerosil 200) and magnesium stearate as a lubricant. The final blend is compressed into the tablets with a conventional rotary press.

Narrative More Specific Description of the Manufacturing Process for the Metformin HCl-Granulate:

a) Metformin HCl is sieved using a screen with a mesh size of 0.5 to 1 mm before weighing.

b) Copolyvidon is dissolved in purified water at ambient temperature with a propeller mixer to produce the "Granulation Liquid"

c) Metformin HCl and corn starch are heated in a chamber of fluid-bed granulator at 70-80° C. for more than 15 min until the product temperature reaches 60° C.

d) The "Granulation Liquid" is sprayed into the mixture for fluid-bed granulating under dry condition to avoid blocking during granulation.

e) At the end of spraying, the resultant granulate is dried at 70-80° C. until the desired LOD value (i.e. 1-2%), in case the LOD is more than 2%.

f) The granulate is sieved using a screen with a mesh size of 0.5 to 1.0 mm.

g) The sieved granulate and colloidal anhydrous silica (Aerosil 200) are blended with a suitable blender. Aerosil 200 should be sieved with a 0.5 mm-screen before use.

h) Magnesium stearate passed through a 0.5 mm sieve and added into the granulate. Subsequently "Final Blend" is produced by final blending in the blender.

i) The "Final Blend" is compressed into the tablets with a conventional rotary press.

Film-coating: The tablets are film-coated by (1) seal-coating: by an aqueous film-coating suspension, containing hypromellose as film-forming agent, propylene glycol as plasticizer, talc as glidant and the pigments yellow iron oxide and/or red iron oxide and titanium dioxide, (2) drug-loading: by an aqueous film-coating suspension, containing hypromellose as film-forming agent, propylene glycol as plasticizer, BI 1356 as drug substance, and L-arginine as stabilizer, and (3) over-coating: by an aqueous film-coating suspension, containing hypromellose as film-forming agent, propylene glycol as plasticizer, talc as glidant and the pigments yellow iron oxide and/or red iron oxide and titanium dioxide.

Narrative More Specific Description of the Manufacturing Process for the Film-Coating with a Coating Machine:

a) Hypromellose and propylene glycol are dissolved in purified water with a propeller mixer. Talc, titanium dioxide, and iron oxide (yellow, red or yellow and red) are dispersed in purified water with a homo-mixer. The suspension is added into the hypromellose solution, then mixed with a propeller mixer at ambient temperature to produce the "Coating Suspension" for "seal-coating" and "over-coating".

b) Hypromellose, propylene glycol and L-arginine are dissolved in purified water with a propeller mixer. BI 1356 (active drug) is added into the hypromellose solution, then dispersed with a propeller mixer at ambient temperature to produce the "Drug Suspension" for "drug-loading".

c) The Metformin HCl tablets are coated with the "Coating Suspension" to the target weight gain to form the "seal-coat". The "Coating Suspension" should be stirred again before use and kept stirring slowly during the coating (spraying) process.

d) Following the seal-coating, the "Drug Suspension" is applied to the surface of the Metformin HCl tablets to form the "drug layer" (drug loading). The "Drug Suspension" should be stirred again before use and kept stirring slowly during the coating (spraying) process. The coating end point can be determined by available PAT (Process Analysis Technology).

e) After drug loading the "Coating Suspension" is applied to the BI 1356 drug-loaded tablets to form the "over-coat" and to produce the "Film-coated Tablets". The "Coating Suspension" should be stirred again before use and kept stirring slowly during the coating (spraying) process.

Product Description:

The product description of BI 1356+Metformin HCl FDC mono-layer tablets (tablet core and film-coated tablets) is shown in Table 8 and Table 9, respectively.

TABLE 8

Product Description of BI 1356 + Metformin HCl
FDC Mono-layer Tablets (Tablet Core)

| | Dose Strength (BI 1356/metformin HCl), mg | | |
|---|---|---|---|
| Items | 2.5/500 | 2.5/850 | 2.5/1000 |
| Tablet shape | Oval, biconvex | Oval, biconvex | Oval, biconvex |
| Tablet size [mm] | 16.2 × 8.5 | 19.1 × 9.3 | 21.0 × 9.6 |
| Color | | white | |
| Weight | 590 | 1000 | 1180 |
| Thickness [mm], (Mean) | Approx. 5.8 | Approx. 7.3 | Approx. 7.6 |
| Crushing strength [N], (Mean) | ≥100, Approx. 140 | ≥150, Approx. 190 | ≥150, Approx. 200 |
| Disintegration time [min] | ≤15 | ≤15 | ≤15 |
| Friability [%] | ≤0.5 | ≤0.5 | ≤0.5 |

TABLE 9

Product Description of BI 1356 + Metformin HCl
FDC Mono-layer Tablets (Coated)

| | Dose Strength (BI 1356/metformin HCl), mg | | |
|---|---|---|---|
| Items | 2.5/500 | 2.5/850 | 2.5/1000 |
| Color | light yellow | light orange | light red |
| Weight | 602 | 1016 | 1198 |
| Thickness [mm], (Mean) | Approx. 5.9 | Approx. 7.4 | Approx. 7.7 |
| Crushing strength [N] (Mean) | ≥100, Approx. 180 | ≥150, Approx. 240 | ≥150, Approx. 250 |
| Disintegration time [min] | ≤15 | ≤15 | ≤15 |

Stability Data:

Stability data of BI 1356+Metformin HCl FDC mono-layer tablets (tablet core) with or without L-arginine is shown in the following tables (over 2 weeks, 1 month and 3 months):

2.5+500 mg tablets+12.5 mg arginine:

| | 60° C. glass bottle | | | |
|---|---|---|---|---|
| Test parameter | Initial | 2 W | 1 M | 3 M |
| Degradation BI 1356 (%) Total | <0.2 | <0.2 | <0.2 | <0.2 |

2.5+500 mg tablets+0 mg arginine:

| | 60° C. glass bottle | | | |
|---|---|---|---|---|
| Test parameter | Initial | 2 W | 1 M | 3 M |
| Degradation BI 1356 (%) Total | <0.2 | 1.1 | 2.9 | 8.5 |

2.5+1000 mg tablets+25 mg arginine:

| | 60° C. glass bottle | | | |
|---|---|---|---|---|
| Test parameter | Initial | 2 W | 1 M | 3 M |
| Degradation BI 1356 (%) Total | <0.2 | <0.2 | <0.2 | 0.2 |

2.5+1000 mg tablets+0 mg arginine:

| | 60° C. glass bottle | | | |
|---|---|---|---|---|
| Test parameter | Initial | 2 W | 1 M | 3 M |
| Degradation BI 1356 (%) Total | 0.2 | 1.9 | 4.7 | 13.6 |

The invention claimed is:

1. A stable pharmaceutical composition comprising a dipeptidyl peptidase-4 (DPP-4) inhibitor which is 1-[(4-methyl-quinazolin-2-yl)methyl]-3-methyl-7-(2-butyn-1-yl)-8-(3-(R)-amino-piperidin-1-yl)-xanthine free base, a partner drug which is metformin hydrochloride, one or more pharmaceutical excipients, and a stabilizing agent for stabilizing said DPP-4 inhibitor against degradation to form an impurity and/or degradation product caused by reaction of the primary amino group of 1-[(4-methyl-quinazolin-2-yl)methyl]-3-methyl-7-(2-butyn-1-yl)-8-(3-(R)-amino-piperidin-1-yl)-xanthine free base when combined with metformin hydrochloride in the composition;
    wherein the stabilizing agent is a nucleophilic and/or basic agent or a buffering agent that is a basic amino acid having an intramolecular amino group and alkaline characteristics;
    wherein the pharmaceutical composition is bioequivalent to the free combination of the DPP-4 inhibitor and metformin hydrochloride;
    wherein the DPP-4 inhibitor is present in a dosage range from 0.5 mg to 10 mg, and the stabilizing agent is present in an amount minimized to not alter the bioequivalence of the pharmaceutical composition to the free combination but sufficient to stabilize said DPP-4 inhibitor against degradation, and
    wherein the impurity and/or degradation product is an N-acetyl or N-carbamoyl derivative of the free base DPP-4 inhibitor.

2. The pharmaceutical composition according to claim 1, wherein the stabilizing agent is the buffering agent.

3. The pharmaceutical composition according to claim 1, wherein said DPP-4 inhibitor is stabilized against chemical degradation.

4. The pharmaceutical composition according to claim 1, wherein the basic amino acid having an intramolecular amino group and alkaline characteristics is selected from the group consisting of L-arginine, L-lysine and L-histidine.

5. The pharmaceutical composition according to claim 1, wherein the DPP-4 inhibitor is present in a dosage strength of 0.5, 1, 2.5, 5 or 10 mg; or wherein the DPP-4 inhibitor is present in a dosage strength of 2.5 mg.

6. The pharmaceutical composition according to claim 1, wherein the metformin hydrochloride is present in a dosage range from about 100 mg to about 1500 mg; or wherein the metformin hydrochloride is present in a dosage strength of 250, 500, 625, 750, 850 or 1000 mg; or wherein the metformin hydrochloride is present in a dosage strength of 500 mg, 850 mg or 1000 mg.

7. The pharmaceutical composition according to claim 1, wherein the nucleophilic and/or basic agent or the buffering agent is L-arginine.

8. The pharmaceutical composition according to claim 7, wherein L-arginine is present from about 1 mg to about 50 mg, or from about 1 mg to about 25 mg.

9. The pharmaceutical composition according to claim 7, wherein the DPP-4 inhibitor and L-arginine are present in a weight ratio from about 1:20 to about 10:1, or from about 1:15 to about 10:1, or from about 1:10 to about 10:1.

10. The pharmaceutical composition according to claim 1, wherein the excipients are selected from the group consisting of:

one or more fillers selected from the group consisting of D-mannitol, corn starch and pregelatinized starch;

a binder which is copovidone;

a lubricant which is magnesium stearate; and a glidant which is colloidal anhydrous silica.

11. The pharmaceutical composition according to claim 1, further comprising copovidone as binder; and optionally one or more of the following: a filler which is corn starch, a lubricant which is magnesium stearate, and a glidant which is colloidal anhydrous silica.

12. The pharmaceutical composition according to claim 1, wherein the composition is in the dosage form of a tablet; wherein the tablet is selected from the group consisting of a mono-layer tablet, a bi-layer tablet, a press-coated tablet, and a tablet which is film-coated for drug-loading.

13. The pharmaceutical composition according to claim 12, wherein the tablet comprises a film-coat.

14. The pharmaceutical composition according to claim 13, wherein the film-coat comprises:

a film-coating agent;

a plasticizer;

optionally a glidant, and optionally one or more pigments.

15. The pharmaceutical composition according to claim 12, wherein the composition is an immediate release dosage form, characterized in that in a dissolution test after 45 minutes at least 75% by weight of each of the DPP-4 inhibitor and partner drug is dissolved.

16. The pharmaceutical composition according to claim 1, wherein the pharmaceutical composition is in the dosage form of a coated tablet, which comprises one or more of the following amounts:

36

| | |
|---|---|
| 0.1-0.5% | DPP-4 inhibitor, |
| 47-85% | metformin HCl, |
| 0.07-2.2% | L-arginine, |
| 3.9-8.1% | binder, |
| 2.3-5.9% | first filler, |
| 0-4.4% | second filler, |
| 0-33% | third filler, |
| 0.7-1.5% | lubricant, and |
| 0.1-0.5% | glidant; | each % by weight of total coated tablet mass.

17. The pharmaceutical composition according to claim 1, wherein the 1-[(4-Methyl-quinazolin-2-yl)methyl]-3-methyl-7-(2-butyn-1-yl)-8-(3-(R)-amino-piperidin-1-yl)-xanthine free base has a particle size distribution of X90<200 µm.

18. The pharmaceutical composition according to claim 17, wherein the 1-[(4-Methyl-quinazolin-2-yl)methyl]-3-methyl-7-(2-butyn-1-yl)-8-(3-(R)-amino-piperidin-1-yl)-xanthine free base has a particle size distribution of X90≤50 µm.

19. The pharmaceutical composition according to claim 17, wherein the 1-[(4-Methyl-quinazolin-2-yl)methyl]-3-methyl-7-(2-butyn-1-yl)-8-(3-(R)-amino-piperidin-1-yl)-xanthine free base has a particle size distribution of 10 µm≤X90≤50 µm.

20. The pharmaceutical composition according to claim 1, wherein the composition contains about <5%, or about <4%, or about <3%, or less than about 2%, of the individual or total impurity or degradation product(s) by total weight.

21. The pharmaceutical composition according to claim 1, which includes less than 1% of the individual or total impurity or degradation product(s) by total weight.

22. The pharmaceutical composition according to claim 1, which includes less than 0.5% of the individual or total impurity or degradation product(s) by total weight.

23. The pharmaceutical composition according to claim 1, which includes less than 0.2% of the individual or total impurity or degradation product(s) by total weight.

* * * * *